United States Patent
Kumar et al.

(10) Patent No.: US 12,268,144 B2
(45) Date of Patent: Apr. 8, 2025

(54) MELON PLANTS WITH MATURITY INDICATOR

(71) Applicant: Syngenta Crop Protection AG, Basel (CH)

(72) Inventors: Rakesh Kumar, Woodland, CA (US); Marc Oliver, Saint-Sauveur (FR); Jose Ignacio Alvarez Casanueva, Almeria (ES)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/347,720

(22) Filed: Jul. 6, 2023

(65) Prior Publication Data

US 2023/0329176 A1    Oct. 19, 2023

Related U.S. Application Data

(63) Continuation of application No. 18/032,046, filed as application No. PCT/EP2021/079608 on Oct. 26, 2021.

(60) Provisional application No. 63/115,774, filed on Nov. 19, 2020, provisional application No. 63/107,114, filed on Oct. 29, 2020.

(51) Int. Cl.
    *A01H 5/08*     (2018.01)
    *A01H 1/00*     (2006.01)
    *A01H 6/34*     (2018.01)

(52) U.S. Cl.
    CPC ............... *A01H 6/344* (2018.05); *A01H 1/00* (2013.01); *A01H 1/106* (2021.01); *A01H 5/08* (2013.01)

(58) Field of Classification Search
    None
    See application file for complete search history.

(56) References Cited

U.S. PATENT DOCUMENTS

2020/0137975 A1    5/2020    Mills

OTHER PUBLICATIONS

Cleper et al., EST Database, BMC Genomics, vol. 12, No. 1, p. 252, 2011.*
Gonzales et al., BMC Genomics, vol. 11, p. 618, 2010.*
Moreno et al., Theor Appl Genet (2008) 116:589-602.*
International Search Report for International Application No. PCT/EP2021/079608 mailed Feb. 18, 2022.
Pablo Rios et al: "ETHQV6.3 is involved in melon climacteric fruit ripening & is encoded by a NAC domain transcpn. factor"; The Plant Journal; Jun. 22, 2017; pp. 672-673, 676 (ISSN: 0960-7412).
Perpina Gorka et al: "'MAK-10': A Long Shelf-life Charentais Breeding Line Developed by Introgression of a Genomic Region from Makuwa Melon"; Hortscience; vol. 52(11); Nov. 1, 2017; pp. 1633-1638 (ISSN: 0018-5345).
Castro Gabriel et al: "New melon introgression lines in a Piel de Sapo genetic background with desirable agronomical traits from dudaim melons"; Euphytica, Springer NL, Dordrecht; vol. 215(10); Sep. 13, 2019; pp. 1-18 (ISSN: 0014-2336).

* cited by examiner

*Primary Examiner* — Phuong T Bui
(74) *Attorney, Agent, or Firm* — Karen A. Magri

(57) ABSTRACT

The invention relates to novel melon plants producing fruits displaying a combination of a long shelf-life trait as well as a maturity indicator trait. The invention also relates to seeds and parts of said plants, for example fruits. The invention further relates to methods of making and using such seeds and plants. The invention also relates to novel genetic sequences associated with a rind-turning phenotype at maturity, which, when combined with a long shelf-life allele, significantly alters the characteristics of the maturing melon fruit, functions as a reliable maturity indicator while retaining suitable marketable features and results in a novel melon plant type.

19 Claims, No Drawings

Specification includes a Sequence Listing.

SEQUENCE LISTING

```
Sequence total quantity: 55
SEQ ID NO: 1                moltype = DNA   length = 179
FEATURE                     Location/Qualifiers
variation                   167
                            note = n is a, c, g, or t
source                      1..179
                            mol_type = genomic DNA
                            organism = Cucumis melo
SEQUENCE: 1
taggagcaag ttcacacgat cctctcgtcc aacctatgtc actattaaat gcacctacat   60
agaaagacca aacaatttct aaagttagaa ggccaacccc aaatcccgta cgtcaagatg  120
aaaggaatca tcaacattcg caagaaggta acgattcata tccaganaaa cctcaaata   179

SEQ ID NO: 2                moltype = DNA   length = 23
FEATURE                     Location/Qualifiers
misc_feature                1..23
                            note = Synthetic
source                      1..23
                            mol_type = other DNA
                            organism = Synthetic construct
SEQUENCE: 2
cctctcgtcc aacctatgtc act                                           23

SEQ ID NO: 3                moltype = DNA   length = 21
FEATURE                     Location/Qualifiers
misc_feature                1..21
                            note = Synthetic
source                      1..21
                            mol_type = other DNA
                            organism = Synthetic construct
SEQUENCE: 3
atgcacctac atagaaagac c                                             21

SEQ ID NO: 4                moltype = DNA   length = 20
FEATURE                     Location/Qualifiers
misc_feature                1..20
                            note = Synthetic
source                      1..20
                            mol_type = other DNA
                            organism = Synthetic construct
SEQUENCE: 4
atgcacctac atggaaagac                                               20

SEQ ID NO: 5                moltype = DNA   length = 23
FEATURE                     Location/Qualifiers
misc_feature                1..23
                            note = Synthetic
source                      1..23
                            mol_type = other DNA
                            organism = Synthetic construct
SEQUENCE: 5
atgaatcgtt accttcttgc gaa                                           23

SEQ ID NO: 6                moltype = DNA   length = 135
FEATURE                     Location/Qualifiers
source                      1..135
                            mol_type = genomic DNA
                            organism = Cucumis melo
SEQUENCE: 6
caagcccagt gcatgaaaga gaattgcggc tttggctagt gacattgatt ctacgactgt   60
gtagggtgac gtgtttgtaa tgggatgaag atcaacaaac atttccagct cctcctcgtt  120
gaattccaaa tcttc                                                   135

SEQ ID NO: 7                moltype = DNA   length = 21
FEATURE                     Location/Qualifiers
misc_feature                1..21
                            note = Synthetic
source                      1..21
                            mol_type = other DNA
                            organism = Synthetic construct
SEQUENCE: 7
gaattgcggc tttggctagt g                                             21

SEQ ID NO: 8                moltype = DNA   length = 20
FEATURE                     Location/Qualifiers
misc_feature                1..20
                            note = Synthetic
source                      1..20
```

```
                        mol_type = other DNA
                        organism = Synthetic construct
SEQUENCE: 8
cattgattct acgactgtgt                                               20

SEQ ID NO: 9            moltype = DNA   length = 21
FEATURE                 Location/Qualifiers
misc_feature            1..21
                        note = Synthetic
source                  1..21
                        mol_type = other DNA
                        organism = Synthetic construct
SEQUENCE: 9
cattgattct acaactgtgt a                                             21

SEQ ID NO: 10           moltype = DNA   length = 23
FEATURE                 Location/Qualifiers
misc_feature            1..23
                        note = Synthetic
source                  1..23
                        mol_type = other DNA
                        organism = Synthetic construct
SEQUENCE: 10
ggaggagctg gaaatgtttg ttg                                           23

SEQ ID NO: 11           moltype = DNA   length = 168
FEATURE                 Location/Qualifiers
source                  1..168
                        mol_type = genomic DNA
                        organism = Cucumis melo
SEQUENCE: 11
cctaaagcac tgagatattc ttggtacaca aggaaaacgt tagcctccca agtcccatct   60
atgtgataac aaacacaaga gatatggctg cttaattata actatgggat tgataatggt  120
gttttgttcg ttaaagagat gatccaccac cataagttcc aaagagaa               168

SEQ ID NO: 12           moltype = DNA   length = 24
FEATURE                 Location/Qualifiers
misc_feature            1..24
                        note = Synthetic
source                  1..24
                        mol_type = other DNA
                        organism = Synthetic construct
SEQUENCE: 12
ttggtacaca aggaaaacgt tagc                                          24

SEQ ID NO: 13           moltype = DNA   length = 19
FEATURE                 Location/Qualifiers
misc_feature            1..19
                        note = Synthetic
source                  1..19
                        mol_type = other DNA
                        organism = Synthetic construct
SEQUENCE: 13
tcccatctat gtgataaca                                                19

SEQ ID NO: 14           moltype = DNA   length = 23
FEATURE                 Location/Qualifiers
misc_feature            1..23
                        note = Synthetic
source                  1..23
                        mol_type = other DNA
                        organism = Synthetic construct
SEQUENCE: 14
aagtcccatc tatgtaataa caa                                           23

SEQ ID NO: 15           moltype = DNA   length = 24
FEATURE                 Location/Qualifiers
misc_feature            1..24
                        note = Synthetic
source                  1..24
                        mol_type = other DNA
                        organism = Synthetic construct
SEQUENCE: 15
ggtggatcat ctctttaacg aaca                                          24

SEQ ID NO: 16           moltype = DNA   length = 122
FEATURE                 Location/Qualifiers
source                  1..122
                        mol_type = genomic DNA
```

```
                        organism = Cucumis melo
SEQUENCE: 16
gcctgagctc gaaatcccag cattgcctgg cgcacaaaac acagcatcgc aggaaggaga    60
gcgctgcaat gcatagcaaa gagcatgttc tcgccctcct ccaccaatca ccaatacaat   120
aa                                                                  122

SEQ ID NO: 17           moltype = DNA   length = 18
FEATURE                 Location/Qualifiers
misc_feature            1..18
                        note = Synthetic
source                  1..18
                        mol_type = other DNA
                        organism = Synthetic construct
SEQUENCE: 17
cattgcctgg cgcacaaa                                                  18

SEQ ID NO: 18           moltype = DNA   length = 16
FEATURE                 Location/Qualifiers
misc_feature            1..16
                        note = Synthetic
source                  1..16
                        mol_type = other DNA
                        organism = Synthetic construct
SEQUENCE: 18
cacagcatcg caggaa                                                    16

SEQ ID NO: 19           moltype = DNA   length = 19
FEATURE                 Location/Qualifiers
misc_feature            1..19
                        note = Synthetic
source                  1..19
                        mol_type = other DNA
                        organism = Synthetic construct
SEQUENCE: 19
acacagcatc acaggaagg                                                 19

SEQ ID NO: 20           moltype = DNA   length = 18
FEATURE                 Location/Qualifiers
misc_feature            1..18
                        note = Synthetic
source                  1..18
                        mol_type = other DNA
                        organism = Synthetic construct
SEQUENCE: 20
ggaggagggc gagaacat                                                  18

SEQ ID NO: 21           moltype = DNA   length = 146
FEATURE                 Location/Qualifiers
variation               19
                        note = n is a, c, g, or t
variation               43
                        note = n is a, c, g, or t
variation               130
                        note = n is a, c, g, or t
source                  1..146
                        mol_type = genomic DNA
                        organism = Cucumis melo
SEQUENCE: 21
tctgatagtc atttgatant tatgtgattg ctatttgatt ganttttaa accttaaggg     60
caagggtaat tgcaaatttg tcaaaaacat ttgaaaaaat taggcccata gcccaaagtt   120
tgcttttttn cgacaaaatt agaaat                                        146

SEQ ID NO: 22           moltype = DNA   length = 22
FEATURE                 Location/Qualifiers
misc_feature            1..22
                        note = Synthetic
source                  1..22
                        mol_type = other DNA
                        organism = Synthetic construct
SEQUENCE: 22
tatgtgattg ctatttgatt ga                                             22

SEQ ID NO: 23           moltype = DNA   length = 14
FEATURE                 Location/Qualifiers
misc_feature            1..14
                        note = Synthetic
source                  1..14
                        mol_type = other DNA
                        organism = Synthetic construct
```

```
SEQUENCE: 23
cccttgccct taag                                                        14

SEQ ID NO: 24          moltype = DNA  length = 14
FEATURE                Location/Qualifiers
misc_feature           1..14
                       note = Synthetic
source                 1..14
                       mol_type = other DNA
                       organism = Synthetic construct
SEQUENCE: 24
cccttgccct taag                                                        14

SEQ ID NO: 25          moltype = DNA  length = 20
FEATURE                Location/Qualifiers
misc_feature           1..20
                       note = Synthetic
source                 1..20
                       mol_type = other DNA
                       organism = Synthetic construct
SEQUENCE: 25
aaagcaaact ttgggctatg                                                  20

SEQ ID NO: 26          moltype = DNA  length = 164
FEATURE                Location/Qualifiers
variation              20
                       note = n is a, c, g, or t
variation              102
                       note = n is a, c, g, or t
variation              110
                       note = n is a, c, g, or t
source                 1..164
                       mol_type = genomic DNA
                       organism = Cucumis melo
SEQUENCE: 26
cccttgctgc atatccagcn gccactccac ctccaagaat caaatatttg aaacagttgg       60
gaaaaagta gtttccttct tcgagtagct cttttgcctc ancaatcttn tctactacag       120
tccttccata aagataaaca gccactgtga aaagcttcca tttt                       164

SEQ ID NO: 27          moltype = DNA  length = 21
FEATURE                Location/Qualifiers
misc_feature           1..21
                       note = Synthetic
source                 1..21
                       mol_type = other DNA
                       organism = Synthetic construct
SEQUENCE: 27
gccactccac ctccaagaat c                                                21

SEQ ID NO: 28          moltype = DNA  length = 22
FEATURE                Location/Qualifiers
misc_feature           1..22
                       note = Synthetic
source                 1..22
                       mol_type = other DNA
                       organism = Synthetic construct
SEQUENCE: 28
caaaagagct actcgaagaa gg                                               22

SEQ ID NO: 29          moltype = DNA  length = 22
FEATURE                Location/Qualifiers
misc_feature           1..22
                       note = Synthetic
source                 1..22
                       mol_type = other DNA
                       organism = Synthetic construct
SEQUENCE: 29
aggcaaaaga gctacttgaa ga                                               22

SEQ ID NO: 30          moltype = DNA  length = 25
FEATURE                Location/Qualifiers
misc_feature           1..25
                       note = Synthetic
source                 1..25
                       mol_type = other DNA
                       organism = Synthetic construct
SEQUENCE: 30
tggctgttta tctttatgga aggac                                            25
```

```
SEQ ID NO: 31              moltype = DNA   length = 214
FEATURE                    Location/Qualifiers
variation                  13..14
                           note = n is a, c, g, or t
variation                  45
                           note = n is a, c, g, or t
variation                  73
                           note = n is a, c, g, or t
variation                  212
                           note = n is a, c, g, or t
source                     1..214
                           mol_type = genomic DNA
                           organism = Cucumis melo
SEQUENCE: 31
cattattatc ccnngaggtt gtggatgatt gaaattgatt gtaanaacta ttttgaatat  60
atagcttatt ttnttagcat ttgttatgta gttataagat atgaactttg atatgatttt 120
tatctttgtt ttctttattt tttagttgta ccctcttaag gaagagatag ttctttcatt 180
ctcacagagc tcagataaat ttccttttta tntt                             214

SEQ ID NO: 32              moltype = DNA   length = 21
FEATURE                    Location/Qualifiers
misc_feature               1..21
                           note = Synthetic
source                     1..21
                           mol_type = other DNA
                           organism = Synthetic construct
SEQUENCE: 32
gtggatgatt gaaattgatt g                                            21

SEQ ID NO: 33              moltype = DNA   length = 22
FEATURE                    Location/Qualifiers
misc_feature               1..22
                           note = Synthetic
source                     1..22
                           mol_type = other DNA
                           organism = Synthetic construct
SEQUENCE: 33
tatgtagtta taagatatga ac                                           22

SEQ ID NO: 34              moltype = DNA   length = 21
FEATURE                    Location/Qualifiers
misc_feature               1..21
                           note = Synthetic
source                     1..21
                           mol_type = other DNA
                           organism = Synthetic construct
SEQUENCE: 34
agttataaga tatcaacttt g                                            21

SEQ ID NO: 35              moltype = DNA   length = 18
FEATURE                    Location/Qualifiers
misc_feature               1..18
                           note = Synthetic
source                     1..18
                           mol_type = other DNA
                           organism = Synthetic construct
SEQUENCE: 35
ctgagctctg tgagaatg                                                18

SEQ ID NO: 36              moltype = DNA   length = 180
FEATURE                    Location/Qualifiers
variation                  135
                           note = n is a, c, g, or t
variation                  174..178
                           note = n is a, c, g, or t
source                     1..180
                           mol_type = genomic DNA
                           organism = Cucumis melo
SEQUENCE: 36
aagtcgctat ttttctaaag tggatgaaca tctgaagtca aggatacaac gatctcaata  60
cagaagagaa aactatagct ttcagatcca tgaacaaaac agaaaacaaa agcaaacggt 120
tatcaattgg catcnagtcc ctgtctttcc attgccctgt agcaaaaaaa aaannnnnga 180

SEQ ID NO: 37              moltype = DNA   length = 24
FEATURE                    Location/Qualifiers
misc_feature               1..24
                           note = Synthetic
source                     1..24
                           mol_type = other DNA
```

```
                          organism = Synthetic construct
SEQUENCE: 37
tggatgaaca tctgaagtca agga                                              24

SEQ ID NO: 38             moltype = DNA   length = 19
FEATURE                   Location/Qualifiers
misc_feature              1..19
                          note = Synthetic
source                    1..19
                          mol_type = other DNA
                          organism = Synthetic construct
SEQUENCE: 38
tgataaccgt ttgcttttg                                                    19

SEQ ID NO: 39             moltype = DNA   length = 19
FEATURE                   Location/Qualifiers
misc_feature              1..19
                          note = Synthetic
source                    1..19
                          mol_type = other DNA
                          organism = Synthetic construct
SEQUENCE: 39
ttgataaccg tgtgctttt                                                    19

SEQ ID NO: 40             moltype = DNA   length = 21
FEATURE                   Location/Qualifiers
misc_feature              1..21
                          note = Synthetic
source                    1..21
                          mol_type = other DNA
                          organism = Synthetic construct
SEQUENCE: 40
acagggcaat ggaaagacag g                                                 21

SEQ ID NO: 41             moltype = DNA   length = 150
FEATURE                   Location/Qualifiers
variation                 52
                          note = n is a, c, g, or t
variation                 61
                          note = n is a, c, g, or t
variation                 109
                          note = n is a, c, g, or t
source                    1..150
                          mol_type = genomic DNA
                          organism = Cucumis melo
SEQUENCE: 41
agatgaatct gtaagagaat tacaaagata gaaaacgagt ttagaaaaat gntagtccta        60
natatgttta agtaactagc atggtcattt taaaaatagt tcacgtacng tgagaggttg       120
gcagtggatg actgtctggg aagcaaaaga                                       150

SEQ ID NO: 42             moltype = DNA   length = 24
FEATURE                   Location/Qualifiers
misc_feature              1..24
                          note = Synthetic
source                    1..24
                          mol_type = other DNA
                          organism = Synthetic construct
SEQUENCE: 42
tacaaagata gaaaacgagt ttag                                              24

SEQ ID NO: 43             moltype = DNA   length = 19
FEATURE                   Location/Qualifiers
misc_feature              1..19
                          note = Synthetic
source                    1..19
                          mol_type = other DNA
                          organism = Synthetic construct
SEQUENCE: 43
agtaactagc atggtcatt                                                    19

SEQ ID NO: 44             moltype = DNA   length = 16
FEATURE                   Location/Qualifiers
misc_feature              1..16
                          note = Synthetic
source                    1..16
                          mol_type = other DNA
                          organism = Synthetic construct
SEQUENCE: 44
taactagcat ggtcgt                                                       16
```

```
SEQ ID NO: 45         moltype = DNA  length = 16
FEATURE               Location/Qualifiers
misc_feature          1..16
                      note = Synthetic
source                1..16
                      mol_type = other DNA
                      organism = Synthetic construct
SEQUENCE: 45
catccactgc caacct                                                       16

SEQ ID NO: 46         moltype = DNA  length = 254
FEATURE               Location/Qualifiers
variation             4..6
                      note = n is a, c, g, or t
variation             87
                      note = n is a, c, g, or t
variation             98
                      note = n is a, c, g, or t
variation             126
                      note = n is a, c, g, or t
variation             128
                      note = n is a, c, g, or t
variation             138
                      note = n is a, c, g, or t
variation             173
                      note = n is a, c, g, or t
variation             175
                      note = n is a, c, g, or t
source                1..254
                      mol_type = genomic DNA
                      organism = Cucumis melo
SEQUENCE: 46
aagnnntttt ttttgtctta gacagttaga gatagattgc tatctttgtc tatccaatag        60
ataaagatat caatttattt gttcctntct cagatagnca ttgatagatt gatatctata      120
tatatntnat gtatacanag attgaaatct atttcttctt attttattaa ttntncttat      180
ttgtgttatg tattacgttg atccaataag tacaactgaa taccaagtaa cggatggaaa      240
ttaacagttt attg                                                        254

SEQ ID NO: 47         moltype = DNA  length = 22
FEATURE               Location/Qualifiers
misc_feature          1..22
                      note = Synthetic
source                1..22
                      mol_type = other DNA
                      organism = Synthetic construct
SEQUENCE: 47
gacagttaga gatagattgc ta                                                22

SEQ ID NO: 48         moltype = DNA  length = 19
FEATURE               Location/Qualifiers
misc_feature          1..19
                      note = Synthetic
source                1..19
                      mol_type = other DNA
                      organism = Synthetic construct
SEQUENCE: 48
acttattgga tcaacgtaa                                                    19

SEQ ID NO: 49         moltype = DNA  length = 19
FEATURE               Location/Qualifiers
misc_feature          1..19
                      note = Synthetic
source                1..19
                      mol_type = other DNA
                      organism = Synthetic construct
SEQUENCE: 49
acttattgga tcaacctaa                                                    19

SEQ ID NO: 50         moltype = DNA  length = 19
FEATURE               Location/Qualifiers
misc_feature          1..19
                      note = Synthetic
source                1..19
                      mol_type = other DNA
                      organism = Synthetic construct
SEQUENCE: 50
tccgttactt ggtattcag                                                    19
```

```
SEQ ID NO: 51         moltype = DNA  length = 214
FEATURE               Location/Qualifiers
variation             46
                      note = n is a, c, g, or t
source                1..214
                      mol_type = genomic DNA
                      organism = Cucumis melo
SEQUENCE: 51
atttataggc catgttaggt caactcagcc ccttacttct acaagnagaa ggaaccatct    60
ctcttttact agtttttaat tcagattgat caccatcatc aagccagaga tgaatatcat   120
ctggcaaatt cgttgacaga aatgagaaaa atatatcatg tttatataga agaacgaatg   180
tccttacata atggcccctt aggttatgcc tcaa                               214

SEQ ID NO: 52         moltype = DNA  length = 25
FEATURE               Location/Qualifiers
misc_feature          1..25
                      note = Synthetic
source                1..25
                      mol_type = other DNA
                      organism = Synthetic construct
SEQUENCE: 52
caactcagcc ccttacttct acaag                                          25

SEQ ID NO: 53         moltype = DNA  length = 16
FEATURE               Location/Qualifiers
misc_feature          1..16
                      note = Synthetic
source                1..16
                      mol_type = other DNA
                      organism = Synthetic construct
SEQUENCE: 53
tcatcaagcc agagat                                                    16

SEQ ID NO: 54         moltype = DNA  length = 17
FEATURE               Location/Qualifiers
misc_feature          1..17
                      note = Synthetic
source                1..17
                      mol_type = other DNA
                      organism = Synthetic construct
SEQUENCE: 54
catcaagcca tagatga                                                   17

SEQ ID NO: 55         moltype = DNA  length = 26
FEATURE               Location/Qualifiers
misc_feature          1..26
                      note = Synthetic
source                1..26
                      mol_type = other DNA
                      organism = Synthetic construct
SEQUENCE: 55
ccattatgta aggacattcg ttcttc                                         26
```

MELON PLANTS WITH MATURITY INDICATOR

RELATED APPLICATION INFORMATION

This application is a continuation of co-pending U.S. application Ser. No. 18/032,046, which claims priority under 35 U.S.C. § 371 from International Application No. PCT/EP2021/079608, filed 26 Oct. 2021, which claims the benefit of U.S. Provisional Application Ser. No. 63/115,774, filed 19 Nov. 2020, and U.S. Provisional Application Ser. No. 63/107,114, filed 29 Oct. 2020, the contents of which are incorporated herein by reference in their entireties.

STATEMENT REGARDING ELECTRONIC SUBMISSION OF A SEQUENCE LISTING

A Sequence Listing in ST26.xml format, submitted under 37 C.F.R. § 1.821, entitled "82194_ST26.xml" 74.9 KB (76,797 bytes) in size, generated on Jul. 3, 2023 and filed via EFS-Web is provided in lieu of a paper copy. This Sequence Listing is hereby incorporated by reference into the specification for its disclosures.

FIELD OF THE INVENTION

The present invention relates to novel melon plants producing fruits displaying a combination of a long shelf-life trait as well as a maturity indicator trait. The present invention also relates to seeds and parts of said plants, for example fruits. The present invention further relates to methods of making and using such seeds and plants. The present invention also relates to novel genetic sequences associated with a rind-turning phenotype at maturity, which, when combined with a long shelf-life allele, significantly alters the characteristics of the maturing melon fruit, functions as a reliable maturity indicator while retaining suitable marketable features and results in a novel melon plant type.

BACKGROUND OF THE INVENTION

Cantaloupe melons that are grown in the Americas have two types of fruit ripening: climacteric and non-climacteric. Traditionally, Western Shipper cantaloupe melons grown in the Americas were climacteric types. Climacteric fruit ripening is characterized by a respiration burst and autocatalytic synthesis of ethylene at the onset of ripening, which triggers a series of ethylene-dependent pathways or processes and the expression of some maturity indicator phenotypes such as the fruit rind turning green to straw/yellow (chlorophyll degradation) and the fruit peduncle slipping from the vines (abscission layer formation, slip type melon), amongst other characters (for a review, Pech et al., 2008). The change of fruit rind colour from green to yellow/straw can therefore serve as an indicator of maturity in this melon type and harvesters can pull fruit from the stem when the rind colour turns and the fruit slips from the vine.

On one hand, these Western Shipper cantaloupe melons have high aroma and musky flavour. They are therefore highly appreciated by the end consumers. However, one disadvantage of this melon type is that they require frequent harvesting (10-12 times), almost every day for two weeks, and is thus labour intensive. Indeed, if they are not picked at full slip stage, subsequent delay reduces fruit shelf life. Furthermore, due to the rise in ethylene production, they also exhibit poor post-harvest shelf life as well as waste due to shrinkage in transit or in storage.

As a result, the traditional Western Shipper cantaloupe (of climacteric type) presence which was prevalent in the most important growing regions as well as in most stores started to decline about 10-12 years ago. They were progressively replaced by long shelf life cantaloupe melons (of non-climacteric type) which are now the common place melon available in most Americas markets. Long shelf life cantaloupe melons (also called harpers) have delivered benefits for both growers and retailers: growers can reduce the number of harvest passes and gain flexibility while retailers have extended shelf life and reduced loss due to shrinkage. A single dominant gene (hereinbelow referred to as LSL10) contributes to long shelf life in most of these melons. These types of melon comprising the LSL10 allele exhibit non-climacteric fruit ripening, with decreased level of and/or sensitivity to ethylene, hence the fruit has excellent field and post-harvest shelf life. Fruit only needs to be picked two-three times as opposed to 10-12 times.

However, the long shelf life cantaloupe melons do not slip from the vine, and their rind colour does not turn from green to yellow upon maturity like they do in traditional Western Shipper varieties. It is thus challenging for the growers to identify the ideal maturity harvest point since they lack a reliable "maturity indicator" such as the rind-turning phenotype, and some melons are therefore harvested before full ripeness and lack aroma and flavour.

Consequently, while the introduction of long shelf life type of cantaloupe melons little over a decade ago resulted in most of commercial growers switching to long shelf life melons due to the several agronomic advantages described above, the end consumer simultaneously started to move away from such melons exhibiting depreciated organoleptic properties. In other words, there is still an unmet need for novel melon types which could satisfy both the growers and retailers on one side, and the consumers on the other side.

SUMMARY OF THE INVENTION

The present invention addresses the need for a novel and improved melon type combining characteristics favourable to both growers and retailers on one end, and consumers on the other end. By identifying one QTL associated with an ethylene-independent rind-turning phenotype and by introgressing its corresponding sequence into long shelf life cantaloupe melon plant backgrounds, the inventors have obtained a novel melon plant type exhibiting long shelf life as well as a maturity indicator trait, which allows growers to harvest melon fruits at the right maturity with minimized labour costs, retailers to yet benefit from a preserved long shelf life characteristic and consumers to enjoy fully matured melon fruits. The rind-turning QTL and its underlying introgressed sequence, located on chromosome 6 (also referred to as rind-turning QTL or QTL6), is of semi-dominant nature, hence one copy of the sequence already provides the rind-turning, maturity indicator phenotype in melon backgrounds harbouring at least one copy of the long shelf life, LSL10 allele.

Altogether, the characteristics of the improved melon plant disclosed within the present invention provide a melon grower with novel solutions to enhance economic and commercial efficiency when deploying cantaloupe melon varieties in the marketplace.

In a first embodiment, the invention provides a cultivated melon plant, preferably a cultivated cantaloupe melon plant, more preferably a *Cucumis melo* var. *cantalupensis* plant or a *Cucumis melo* var. *reticulatus* plant comprising in its genome:

a) at least one copy of an LSL10 allele, and;
b) at least one copy of an introgressed sequence from *C. melo* var. *dudaim* associated with the rind-turning phenotype, located on chromosome 6 and comprising at least one of the following SNP markers:
   i) an A genotype in the heterozygous or homozygous state for SNP marker 1 at a position corresponding to position 61 in SEQ ID NO: 1;
   ii) a G genotype in the heterozygous or homozygous state for SNP marker 2 at a position corresponding to position 55 in SEQ ID NO: 6;
   iii) a G genotype in the heterozygous or homozygous state for SNP marker 3 at a position corresponding to position 65 in SEQ ID NO: 11;
   iv) a G genotype in the heterozygous or homozygous state for SNP marker 4 at a position corresponding to position 49 in SEQ ID NO: 16;
   v) a C genotype in the heterozygous or homozygous state for SNP marker 5 at a position corresponding to position 53 in SEQ ID NO: 21;
   vi) a G genotype in the heterozygous or homozygous state for SNP marker 6 at a position corresponding to position 83 in SEQ ID NO: 26;
   vii) a G genotype in the heterozygous or homozygous state for SNP marker 7 at a position corresponding to position 103 in SEQ ID NO: 31;
   viii) an A genotype in the heterozygous or homozygous state for SNP marker 8 at a position corresponding to position 115 in SEQ ID NO: 36;
   ix) an A genotype in the heterozygous or homozygous state for SNP marker 9 at a position corresponding to position 87 in SEQ ID NO: 41; and/or
   x) a C genotype in the heterozygous or homozygous state for SNP marker 10 at a position corresponding to position 196 in SEQ ID NO: 46;
wherein said plant produces melon fruit exhibiting a long shelf-life phenotype, and wherein said melon fruit further exhibits a rind-turning phenotype when reaching full maturity.

In a further embodiment, said introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41 and/or SEQ ID NO: 46, or a sequence that is at least 80%, preferably at least 85%, more preferably at least 90%, even more preferably at least 95% identical to one or more of said sequences.

In a further embodiment, the invention provides a plant according to any one of the preceding embodiments, wherein said rind-turning phenotype is characterized by a rind colour turn from green when immature into yellow when reaching full maturity.

In a further embodiment, said melon fruit rind yellow colour at full maturity ranges from 15 to 20 (A-D) when measured using the colour patch of the Royal Horticultural Society Colour Chart.

In a further embodiment, said melon fruit rind yellow colour at full maturity is 19A or 19B when measured using the colour patch of the Royal Horticultural Society Colour Chart.

In a further embodiment, said melon fruit rind green colour when immature ranges from 135 to 143 (A-D) when measured using the colour patch of the Royal Horticultural Society Colour Chart.

In a further embodiment, said melon fruit rind green colour when immature is 138C, 138D or 139A when measured using the colour patch of the Royal Horticultural Society Colour Chart.

In a further embodiment, the rind-turning phenotype is evaluated as disclosed in Example 2A.

In a further embodiment, the invention provides a plant according to any of the preceding embodiments, wherein said LSL10 allele comprises the following SNP marker:
a) a G genotype in the heterozygous or homozygous state for SNP marker 11 at a position corresponding to position 107 in SEQ ID NO: 51.

In a further embodiment, said LSL10 allele comprises SEQ ID NO: 51, or a sequence that is at least 80%, preferably at least 85%, more preferably at least 90%, even more preferably at least 95% identical to said sequence.

In a further embodiment of the invention, said plant is homozygous for said at least one SNP marker 1 to 10. In a further embodiment, the invention provides a plant according to any preceding embodiment, wherein said plant is homozygous for said LSL10 allele.

In a further embodiment of the invention, said LSL10 allele and said introgressed sequence are comprised in melon line 19MNA106815, representative seed of which is deposited under ATCC Accession No. PTA-126875, or a progeny or an ancestor thereof. In a further embodiment, the invention provides a plant according to any of the preceding embodiments wherein said plant is obtained by crossing melon line 19MNA106815, representative seed of which is deposited under ATCC Accession No. PTA-126875, or a progeny or an ancestor thereof, with a melon plant that does not contain said introgressed sequence.

In a further embodiment, the invention provides a plant according to any of the preceding embodiments, wherein said plant is an inbred, a dihaploid or a hybrid plant.

It is a further embodiment to provide a plant part, organ or tissue obtainable from a melon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the rind-turning phenotype according to the invention, particularly when grown into a plant that produces fruits.

In a further embodiment, the invention provides a seed that produces a plant according to any of the preceding embodiments.

In a further embodiment, the invention provides a method for producing a cultivated melon plant, preferably a cultivated Cantaloupe melon plant, more preferably a *Cucumis melo* var. *cantalupensis* plant or a *Cucumis melo* var. *reticulatus* plant, wherein said plant produces melon fruits exhibiting a long shelf-life phenotype as well as a rind-turning phenotype when reaching full maturity, wherein the method comprising the steps of
a) crossing a plant according to any one of the preceding embodiments with a cultivated melon plant lacking said LSL10 allele and said introgressed sequence;
b) selecting a progeny plant comprising at least one copy of an LSL10 allele and at least one copy of an introgressed sequence from *C. melo* var. *dudaim* located on chromosome 6, said selecting step comprising detecting at least one of the following SNP markers:
   i) an A genotype in the heterozygous or homozygous state for SNP marker 1 at a position corresponding to position 61 in SEQ ID NO: 1;

ii) a G genotype in the heterozygous or homozygous state for SNP marker 2 at a position corresponding to position 55 in SEQ ID NO: 6;
iii) a G genotype in the heterozygous or homozygous state for SNP marker 3 at a position corresponding to position 65 in SEQ ID NO: 11;
iv) a G genotype in the heterozygous or homozygous state for SNP marker 4 at a position corresponding to position 49 in SEQ ID NO: 16;
v) a C genotype in the heterozygous or homozygous state for SNP marker 5 at a position corresponding to position 53 in SEQ ID NO: 21;
vi) a G genotype in the heterozygous or homozygous state for SNP marker 6 at a position corresponding to position 83 in SEQ ID NO: 26;
vii) a G genotype in the heterozygous or homozygous state for SNP marker 7 at a position corresponding to position 103 in SEQ ID NO: 31;
viii) an A genotype in the heterozygous or homozygous state for SNP marker 8 at a position corresponding to position 115 in SEQ ID NO: 36;
ix) an A genotype in the heterozygous or homozygous state for SNP marker 9 at a position corresponding to position 87 in SEQ ID NO: 41; and/or
x) a C genotype in the heterozygous or homozygous state for SNP marker 10 at a position corresponding to position 196 in SEQ ID NO: 46;

thereby producing a plant producing fruits with a long shelf-life phenotype as well as a rind-turning phenotype when reaching full maturity.

In a further embodiment, the invention relates to the method of any of the preceding embodiments, wherein the method further comprises:
c) selfing the selected progeny or crossing the selected progeny with another melon plant to produce further progeny.

In a further embodiment, the invention relates to the method of the preceding embodiment, wherein further progeny is selected and selfed/crossed for 2 to 10 more generations.

In a further embodiment, the invention relates to the method of any of the preceding embodiments, wherein the plant of step a) is melon line 19MNA106815, representative seed of which is deposited under ATCC Accession No. PTA-126875, or a progeny or an ancestor thereof.

In a further embodiment, the invention relates to a method for producing a F1 melon plant exhibiting a rind-turning phenotype, the method comprising crossing an inbred melon plant, which is a plant according to any one of the preceding embodiments, with a different inbred melon plant to produce F1 hybrid progeny.

In a further embodiment, the invention provides a method for identifying a cultivated melon plant, preferably a cultivated Cantaloupe melon plant, more preferably a *Cucumis melo* var. *reticulatus* plant or a *Cucumis melo* var. *cantalupensis* plant, wherein said plant produces melon fruits exhibiting a long shelf life phenotype as well as a rind-turning phenotype when reaching full maturity, wherein said plant comprises at least one copy of an LSL10 allele and at least one copy of an introgressed sequence from *C. melo* var. *dudaim* located on chromosome 6, wherein said method comprising the step of detecting at least one of the following SNP markers:
a) an A genotype in the heterozygous or homozygous state for SNP marker 1 at a position corresponding to position 61 in SEQ ID NO: 1;
b) a G genotype in the heterozygous or homozygous state for SNP marker 2 at a position corresponding to position 55 in SEQ ID NO: 6;
c) a G genotype in the heterozygous or homozygous state for SNP marker 3 at a position corresponding to position 65 in SEQ ID NO: 11;
d) a G genotype in the heterozygous or homozygous state for SNP marker 4 at a position corresponding to position 49 in SEQ ID NO: 16;
e) a C genotype in the heterozygous or homozygous state for SNP marker 5 at a position corresponding to position 53 in SEQ ID NO: 21;
f) a G genotype in the heterozygous or homozygous state for SNP marker 6 at a position corresponding to position 83 in SEQ ID NO: 26;
g) a G genotype in the heterozygous or homozygous state for SNP marker 7 at a position corresponding to position 103 in SEQ ID NO: 31;
h) an A genotype in the heterozygous or homozygous state for SNP marker 8 at a position corresponding to position 115 in SEQ ID NO: 36;
i) an A genotype in the heterozygous or homozygous state for SNP marker 9 at a position corresponding to position 87 in SEQ ID NO: 41; and/or
j) a C genotype in the heterozygous or homozygous state for SNP marker 10 at a position corresponding to position 196 in SEQ ID NO: 46;

thereby identifying a melon plant producing fruits with a long shelf-life phenotype as well as a rind-turning phenotype when reaching full maturity.

In a further embodiment, the invention relates to the method of the preceding embodiment, wherein the method further comprises the step of detecting the following SNP marker
a) a G genotype in the heterozygous or homozygous state for SNP marker 11 at a position corresponding to position 107 in SEQ ID NO: 51.

In a further embodiment, the invention relates to the method of any of the preceding embodiments, wherein said method further comprises selecting a melon plant comprising said one or more SNP markers, and crossing the selected melon plant with a second melon plant to produce progeny melon plants that comprise at least one of said SNP markers and exhibits the rind-turning phenotype of the invention.

DETAILED DESCRIPTION OF THE INVENTION

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated melon" or an "elite melon" plant is understood within the scope of the invention to refer to a plant that is no longer in the natural state but has been developed and domesticated by human care and for agricultural use and/or human consumption. In the context of the present invention, a "cultivated melon" or an "elite melon" plant excludes wild melon accessions. As a matter of example, in embodiments, a cultivated or elite melon plant according to the present invention is capable of growing fruits having a Brix level better than 8, preferably better than 10, even more preferably better than 12. Alternatively, or additionally, the cultivated melon plant is a hybrid plant. Alternatively, or additionally, the cultivated melon plant is a cantaloupe melon plant. Alternatively, or additionally, the cultivated cantaloupe melon plant is a *C. melo* var. *cantalupensis* plant or a *C. melo* var. *reticulatus* plant (Pitrat et al., 2000). In the context of an interspecific cross between a *C. melo* var. *cantalupensis* plant or a *C. melo* var. *reticulatus* plant and a wild melon accession, or a different *C. melo* var., for instance a *C. melo* var. *dudaim* accession, a cultivated melon plant is defined as a progeny plant of said interspecific cross, wherein said progeny plant has been backcrossed at least three times against a *C. melo* var. *cantalupensis* plant or a *C. melo* var. *reticulatus* plant.

An "allele" is understood within the scope of the invention to refer to alternative or variant forms of various genetic units identical or associated with different forms of a gene or of any kind of identifiable genetic determinant such as a QTL, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

The term "rind-turning" or "rind colour turning" is herein understood to mean that a plant comprising an introgressed sequence from a *C. melo* var. *dudaim* plant located on chromosome 6 and comprising at least one of SNP markers 1 to 10 as well as at least one copy of an LSL10 allele, is exhibiting a rind-turning phenotype when compared with a plant lacking said introgressed sequence. In particular, a melon plant according to the present invention produces fruits exhibiting a rind colour turning from green when immature to straw or yellow when reaching full maturity. In contrast, a plant lacking the introgressed sequence of the invention produces fruits whose rind colour does not turn, i.e., stays green or greyish green, between the immature stage towards the full maturity stage.

An "immature fruit" is understood within the scope of the invention to mean a melon fruit with total soluble solids less than 10° Brix.

"Full maturity" or "fully matured fruit" is understood within the scope of the invention to mean a melon fruit with total soluble solids equal to or greater than 10° Brix, preferably greater than 12° Brix.

The term "long shelf life" phenotype is understood within the scope of the invention to refer to fruits which do not slip from the vine (i.e. do not form an abscission layer) at maturity and/or which, when harvested, retain good marketable characteristics for 14 to 20 days post-harvest.

"Phenotype" is understood within the scope of the invention to refer to a distinguishable characteristic(s) of a genetically controlled trait.

A "control melon plant" is understood within the scope of the invention to mean a melon plant that has the same genetic background as the cultivated melon plant of the present invention wherein the control plant does not have the introgressed sequence linked to the rind-turning phenotype. In particular, a control melon plant is a melon plant belonging to the same plant variety and does not comprise the introgressed sequence of the present invention. In particular, a control melon plant can be a melon plant comprising an LSL10 allele, but which does not comprise the introgressed sequence located on chromosome 6. The control melon plant is grown for the same length of time and under the same conditions as the cultivated melon plant of the present invention. Plant variety is herein understood according to definition of UPOV. Thus, a control melon plant may be a near-isogenic line, an inbred line or a hybrid provided that they have the same genetic background as the melon plant of the present invention except the control plant does not have the introgressed sequence of the present invention linked to the rind-turning phenotype.

The term "trait" refers to a characteristic or a phenotype. In the context of the present invention, the trait is a rind-turning trait. A trait may be inherited in a dominant or recessive manner, or in a partial or incomplete-dominant manner. In the context of the present invention, the rind-turning introgressed sequence located on chromosome 6 is semi-dominant. A melon plant of the invention can therefore be homozygous or heterozygous for the trait. Furthermore, a trait may be monogenic or polygenic, or may result from the interaction of one or more genes with the environment. In the context of the present invention, the rind-turning introgressed sequence located on chromosome 6 confers the rind-turning trait when associated with a long shelf life LSL10 allele.

The terms "hybrid", "hybrid plant", and "hybrid progeny" refer to an individual produced from genetically different parents (e.g., a genetically heterozygous or mostly heterozygous individual).

The term "inbred line" refers to a genetically homozygous or nearly homozygous population. An inbred line, for example, can be derived through several cycles of brother/sister breeding or of selfing or in dihaploid production.

The term "dihaploid line" refers to stable inbred lines issued from anther culture. Some pollen grains (haploid) cultivated on specific medium, and circumstances can develop plantlets containing n chromosomes. These plantlets are then "doubled" and contain 2n chromosomes. The progeny of these plantlets is named "dihaploid" and is essentially no longer segregating (stable).

The term "genetically fixed" refers to a genetic sequence which has been stably incorporated into the genome of a plant that normally does not contain said genetic sequence. When genetically fixed, the genetic sequence can be transmitted in an easy and predictable manner to other plants by sexual crosses.

The term "rootstock" refers to a plant used as a receptacle for a scion plant. Typically, the rootstock plant and the scion plant are of different genotypes. In embodiments, plants according to the present invention are used as rootstock plants.

The term "plant" or "plant part' refers hereinafter to a plant part, organ or tissue obtainable from a melon plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the rind-turning trait according to the invention, particularly when grown into a plant that produces fruits.

A "plant" is any plant at any stage of development.

A melon plant seed is a seed which grows into a melon plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes, and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program, e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively, or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes. In the context of the invention, a melon plant comprising two identical copies of a particular introgressed sequence at a particular locus, e.g., the introgressed sequence located on chromosome 6, is homozygous on a corresponding locus.

"Heterozygous" is understood within the scope of the invention to refer to unlike alleles at one or more corresponding loci on homologous chromosomes. In the context of the invention, a melon plant comprising one copy of a particular introgressed sequence at a particular locus, e.g., the introgressed sequence located on chromosome 6, is heterozygous on a corresponding locus.

A "dominant" allele is understood within the scope of the invention to refer to an allele which determines the phenotype when present in the heterozygous or homozygous state.

A "semi-dominant" allele is understood within the scope of the invention to refer to an allele which determines the phenotype when present in the heterozygous or homozygous state. The intensity of the phenotype is however generally higher when the allele is present in the homozygous state.

A "recessive" allele refers to an allele which determines the phenotype when present in the homozygous state only.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene, a QTL or its corresponding genetic sequence contributing to a trait.

As used herein, "marker locus" refers to a region on a chromosome, which comprises a nucleotide or a polynucleotide sequence that is present in an individual's genome and that is associated with one or more loci of interest, which may comprise a gene or any other genetic determinant or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. The term "associated with" can be used with an equal meaning.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments, fertilization of one individual by another (e.g., cross-pollination in plants). The term "selfing" refers in some embodiments to the production of seed by self-fertilization or self-pollination, i.e., pollen and ovule are from the same plant.

As used herein, the phrase "genetic marker" or "DNA marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

As used herein, the term "genotype" refers to the genetic constitution of a cell or organism. An individual's "genotype for a set of genetic markers" includes the specific alleles, for one or more genetic marker loci, present in the individual's haplotype.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the terms "quantitative trait locus" (QTL) refer to an association between a genetic marker and a chromosomal region and/or gene and/or introgressed sequence that affects the phenotype of a trait of interest. Typically, this is determined statistically, e.g., based on one or more methods published in the literature. A QTL can be a chromosomal region and/or a genetic locus with at least two alleles that differentially affect a phenotypic trait.

The term "recipient melon plant" is used herein to indicate a melon plant that is to receive DNA obtained from a donor melon plant that comprises an introgressed sequence for the rind-turning trait. In the context of the present invention, the recipient plant may already comprise at least one copy of an LSL10 allele, in such case introgression of at least one copy of QTL6 is necessary for the expression of the rind-turning phenotype. In the context of the present invention, the recipient plant may also be a plant lacking both QTL6 and an LSL10 allele, so that the introgression of at least one copy of each is necessary for the expression of the rind-turning phenotype.

The term "natural genetic background" is used herein to indicate the original genetic background of genetic sequence. Such a background may for instance be the genome of a wild accession of melon. For instance, the genetic sequence of the present invention was found at a specific location on chromosome 6 of a *C. melo* var. *dudaim* plant. Conversely, a method that involves the transfer of DNA, via e.g., breeding, comprising this genetic sequence from chromosome 6 of *C. melo* var. *dudaim* plant to the same position on chromosome 6 of another melon species, preferably a cultivated melon plant or a cultivated cantaloupe melon plant, even more preferably a *C. melo* var. *cantalupensis* plant or a *C. melo* var. *reticulatus* plant, will result in this genetic sequence not being in its natural genetic background. When the genetic sequence of the present invention is transferred from a *C. melo* var. *dudaim* background into another melon species, preferably a cultivated melon plant, even more preferably a *C. melo* var. *cantalupensis* or *C. melo* var. *reticulatus* plant, they are referred to as "introgressed sequence" or "introgressed genetic sequence".

A "donor melon plant" is understood within the scope of the invention to mean the melon plant which provides, at least, the introgressed sequence for rind-turning. In the context of the present invention, if the recipient plant lacks at least one copy of an LSL10 allele, then the donor plant may also comprise such at least one copy of an LSL10 allele.

"Marker-based selection" is understood within the scope of the invention to refer to e.g. the use of genetic markers to detect one or more nucleic acids from the plant, where the nucleic acid is associated with a desired trait to identify plants that carry alleles for desirable (or undesirable) traits, so that those plants can be used (or avoided) in a selective breeding program.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (i.e., amplified sequence or target), one or more labelled allele-specific oligonucleotide probes and a detection system that records and interprets the hybridization signal. The presence or absence of the desired SNP marker allele may be determined by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions. "PCR primer" is understood within the scope of the invention to refer to relatively short fragments of single-stranded DNA used in the PCR amplification of specific regions of DNA.

"Probe" as used herein refers to a group of atoms or molecules which can recognise and bind to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

"Sequence Identity". The terms "identical" or "identity" in the context of two or more nucleic acid or protein sequences, refer to two or more sequences or sub-sequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), considering the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, WI 53711). Bestfit utilizes the local homology algorithm of Smith and Waterman, Advances in Applied Mathematics 2 (1981), 482-489, to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their pre-set ("default") values. The deviations appearing in the comparison between a given sequence and the above-described sequence of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

EMBODIMENTS

Plants, Seeds, Fruits.

In a first embodiment, the invention provides a cultivated melon plant, preferably a cultivated cantaloupe melon plant, more preferably a *Cucumis melo* var. *cantalupensis* plant or a *Cucumis melo* var. *reticulatus* plant comprising in its genome:
- a) at least one copy of an LSL10 allele, and;
- b) at least one copy of an introgressed sequence from *C. melo* var. *dudaim* associated with the rind-turning phenotype, located on chromosome 6 and comprising at least one of the following SNP markers:
  - i) an A genotype in the heterozygous or homozygous state for SNP marker 1 in SEQ ID NO: 1;
  - ii) a G genotype in the heterozygous or homozygous state for SNP marker 2 in SEQ ID NO: 6;
  - iii) a G genotype in the heterozygous or homozygous state for SNP marker 3 in SEQ ID NO: 11;
  - iv) a G genotype in the heterozygous or homozygous state for SNP marker 4 in SEQ ID NO: 16;
  - v) a C genotype in the heterozygous or homozygous state for SNP marker 5 in SEQ ID NO: 21;
  - vi) a G genotype in the heterozygous or homozygous state for SNP marker 6 in SEQ ID NO: 26;
  - vii) a G genotype in the heterozygous or homozygous state for SNP marker 7 in SEQ ID NO: 31;
  - viii) an A genotype in the heterozygous or homozygous state for SNP marker 8 in SEQ ID NO: 36;
  - ix) an A genotype in the heterozygous or homozygous state for SNP marker 9 in SEQ ID NO: 41; and/or
  - x) a C genotype in the heterozygous or homozygous state for SNP marker 10 in SEQ ID NO: 46;

wherein said plant produces melon fruit exhibiting a long shelf-life phenotype, and
  wherein said melon fruit further exhibits a rind-turning phenotype when reaching full maturity.

In a further embodiment, the invention provides a cultivated melon plant, preferably a cultivated cantaloupe melon plant, more preferably a *Cucumis melo* var. *cantalupensis* plant or a *Cucumis melo* var. *reticulatus* plant comprising in its genome:
- a) at least one copy of an LSL10 allele, and;
- b) at least one copy of an introgressed sequence from *C. melo* var. *dudaim* associated with the rind-turning phenotype, located on chromosome 6 and comprising at least one of the following SNP markers:
  - i) an A genotype in the heterozygous or homozygous state for SNP marker 1 at a position corresponding to position 61 in SEQ ID NO: 1;
  - ii) a G genotype in the heterozygous or homozygous state for SNP marker 2 at a position corresponding to position 55 in SEQ ID NO: 6;
  - iii) a G genotype in the heterozygous or homozygous state for SNP marker 3 at a position corresponding to position 65 in SEQ ID NO: 11;
  - iv) a G genotype in the heterozygous or homozygous state for SNP marker 4 at a position corresponding to position 49 in SEQ ID NO: 16;
  - v) a C genotype in the heterozygous or homozygous state for SNP marker 5 at a position corresponding to position 53 in SEQ ID NO: 21;
  - vi) a G genotype in the heterozygous or homozygous state for SNP marker 6 at a position corresponding to position 83 in SEQ ID NO: 26;
  - vii) a G genotype in the heterozygous or homozygous state for SNP marker 7 at a position corresponding to position 103 in SEQ ID NO: 31;
  - viii) an A genotype in the heterozygous or homozygous state for SNP marker 8 at a position corresponding to position 115 in SEQ ID NO: 36;
  - ix) an A genotype in the heterozygous or homozygous state for SNP marker 9 at a position corresponding to position 87 in SEQ ID NO: 41; and/or
  - x) a C genotype in the heterozygous or homozygous state for SNP marker 10 at a position corresponding to position 196 in SEQ ID NO: 46;

wherein said plant produces melon fruit exhibiting a long shelf-life phenotype, and
  wherein said melon fruit further exhibits a rind-turning phenotype when reaching full maturity.

Further, the plant of any of the previous embodiments wherein:
- a) the A genotype for SNP marker 1 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;
- b) the G genotype for SNP marker 2 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;
- c) the G genotype for SNP marker 3 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13;
- d) the G genotype for SNP marker 4 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18;
- e) the C genotype for SNP marker 5 can be identified in a PCR by amplification of a nucleic acid fragment with a pair of oligonucleotide primers: forward primer of SEQ ID NO: 22 and reverse primer of SEQ ID NO: 25, and probe of SEQ ID NO: 23;
- f) the G genotype for SNP marker 6 can be identified in a PCR by amplification of a nucleic acid fragment with a pair of oligonucleotide primers: forward primer of SEQ ID NO: 27 and reverse primer of SEQ ID NO: 30, and probe of SEQ ID NO: 28;
g) the G genotype for SNP marker 7 can be identified in a PCR by amplification of a nucleic acid fragment with a pair of oligonucleotide primers: forward primer of SEQ ID NO: 32 and reverse primer of SEQ ID NO: 35, and probe of SEQ ID NO: 33;
h) the A genotype for SNP marker 8 can be identified in a PCR by amplification of a nucleic acid fragment with a pair of oligonucleotide primers: forward primer of SEQ ID NO: 37 and reverse primer of SEQ ID NO: 40, and probe of SEQ ID NO: 38;
i) the A genotype for SNP marker 9 can be identified in a PCR by amplification of a nucleic acid fragment with a pair of oligonucleotide primers: forward primer of SEQ ID NO: 42 and reverse primer of SEQ ID NO: 45, and probe of SEQ ID NO: 43; and/or
j) the C genotype for SNP marker 10 can be identified in a PCR by amplification of a nucleic acid fragment with a pair of oligonucleotide primers: forward primer of SEQ ID NO: 47 and reverse primer of SEQ ID NO: 50, and probe of SEQ ID NO: 48.

In a further embodiment of the invention, said rind-turning introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41 and/or SEQ ID NO: 46, or a sequence that is at least 80%, preferably at least 85%, more preferably at least 90%, even more preferably at least 95% identical to said sequence while retaining the corresponding SNP marker 1 to 10.

In a further embodiment, the invention provides a plant according to any one of the preceding embodiments, wherein said rind-turning phenotype is characterized by a rind colour turn from green when immature into yellow when reaching full maturity.

In a further embodiment, said melon fruit rind yellow colour at full maturity ranges from 15 to 20 (A-D) when measured using the colour patch of the Royal Horticultural Society Colour Chart.

In a further embodiment, said melon fruit rind yellow colour at full maturity is 19A or 19B when measured using the colour patch of the Royal Horticultural Society Colour Chart.

In a further embodiment, said melon fruit rind green colour when immature ranges from 135 to 143 (A-D) when measured using the colour patch of the Royal Horticultural Society Colour Chart.

In a further embodiment, said melon fruit rind green colour when immature is 138C, 138D or 139A when measured using the colour patch of the Royal Horticultural Society Colour Chart.

In a further embodiment, the rind-turning phenotype is evaluated as disclosed in Example 2A.

In a further embodiment, the invention provides a plant according to any of the preceding embodiments, wherein said LSL10 allele comprises the following SNP marker:
a) a G genotype in the heterozygous or homozygous state for SNP marker 11 in SEQ ID NO: 51.

In a further embodiment, the invention provides a plant according to any of the preceding embodiments, wherein said LSL10 allele comprises the following SNP marker:
a) a G genotype in the heterozygous or homozygous state for SNP marker 11 at a position corresponding to position 107 in SEQ ID NO: 51.

Further, the plant of the previous embodiment wherein:
a) the G genotype for SNP marker 11 can be identified in a PCR by amplification of a nucleic acid fragment with a pair of oligonucleotide primers: forward primer of SEQ ID NO: 52 and reverse primer of SEQ ID NO: 55, and probe of SEQ ID NO: 53.

In a further embodiment, said LSL10 allele comprises SEQ ID NO: 51, or a sequence that is at least 80%, preferably at least 85%, more preferably at least 90%, even more preferably at least 95% identical to said allele while retaining corresponding SNP marker 11.

In a further embodiment of the invention, said plant is homozygous for said at least one SNP marker 1 to 10. In a further embodiment, the invention provides a plant according to any preceding embodiment, wherein said plant is homozygous for said LSL10 allele.

In a further embodiment of the invention, said LSL10 allele and said introgressed sequence are comprised in melon line 19MNA106815, representative seed of which is deposited under ATCC Accession No. PTA-126875, or a progeny or an ancestor thereof. In a further embodiment, the invention provides a plant according to any of the preceding embodiments wherein said plant is obtained by crossing melon line 19MNA106815, representative seed of which is deposited under ATCC Accession No. PTA-126875, or a progeny or an ancestor thereof, with a melon plant that does not contain said introgressed sequence.

In a further embodiment, the invention provides a plant according to any of the preceding embodiments, wherein said plant is an inbred, a dihaploid or a hybrid plant.

In another embodiment, the plant according to the invention is male sterile. In another embodiment, the plant according to the invention is cytoplasmic male sterile.

In another embodiment, the plant according to the invention grows mature melon fruits, wherein the interior flesh of said mature fruits is orange.

In a further embodiment, the melon plant of the invention is a melon plant according to any of preceding embodiments, wherein said rind-turning introgressed sequence located on chromosome 6 can be identified using any of the SNP markers 1 to 10 disclosed in Table 4 hereinbelow.

In a further embodiment, the melon plant of the invention is a melon plant according to any of the preceding embodiments, wherein melon line 19MNA106815, or a progeny or an ancestor thereof, is the source of said rind turning introgressed sequence and LSL10 allele, and wherein a representative seed of line 19MNA106815 has been deposited under ATCC Accession No. PTA-126875.

It is a further embodiment to provide a plant part, organ or tissue obtainable from a melon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the rind-turning phenotype according to the invention, particularly when grown into a plant that produces fruits.

In a further embodiment, the invention provides a seed that produces a plant according to any of the preceding embodiments.

In a further embodiment the invention relates to the use of a melon plant according to any of the preceding embodiments as a melon rootstock. In a further embodiment the invention relates to the use of melon line 19MNA106815, representative seed of which is deposited under ATCC Accession No. PTA-126875, or a progeny or an ancestor thereof as a melon rootstock.

In another embodiment is considered the use of a melon plant, plant part or seed according to any of the preceding embodiments for producing and harvesting melon fruits. In another embodiment the invention relates to the use of a melon plant, plant part or seed according to any embodiments, wherein the melon plant, plant part or seed is melon line 19MNA106815, representative seed of which is deposited under ATCC Accession No. PTA-126875, or a progeny or an ancestor thereof.

In a further embodiment, the invention relates to the use of a melon plant, plant part or seed according to any of the preceding embodiments to sow a field, a greenhouse, or a plastic house.

In one embodiment, the invention provides melon fruits produced by a melon plant according to any of the preceding embodiments.

The invention further relates to the use of a melon plant according to any of the preceding embodiments to introgress a rind-turning trait into a melon plant lacking said rind-turning trait.

Genetic Sequences, Markers.

The present invention is further directed to an introgressed genetic sequence linked to the rind-turning trait in a recipient melon plant comprising an LSL10 allele. In a further embodiment, the introgressed genetic sequence of the present invention is located on chromosome 6. In a further embodiment of the present invention, the genetic sequence is comprised in, obtained from or obtainable from a donor plant of melon line 19MNA106815, representative seed of which is deposited under ATCC Accession No. PTA-126875, or a progeny or an ancestor thereof, and comprising said introgressed genetic sequence.

In another embodiment, the introgressed genetic sequence of the present invention is located on chromosome 6 and is characterized by at least one of the following SNP markers:
  a) an A genotype in the heterozygous or homozygous state for SNP marker 1 at a position corresponding to position 61 in SEQ ID NO: 1;
  b) a G genotype in the heterozygous or homozygous state for SNP marker 2 at a position corresponding to position 55 in SEQ ID NO: 6;
  c) a G genotype in the heterozygous or homozygous state for SNP marker 3 at a position corresponding to position 65 in SEQ ID NO: 11;
  d) a G genotype in the heterozygous or homozygous state for SNP marker 4 at a position corresponding to position 49 in SEQ ID NO: 16;
  e) a C genotype in the heterozygous or homozygous state for SNP marker 5 at a position corresponding to position 53 in SEQ ID NO: 21;
  f) a G genotype in the heterozygous or homozygous state for SNP marker 6 at a position corresponding to position 83 in SEQ ID NO: 26;
  g) a G genotype in the heterozygous or homozygous state for SNP marker 7 at a position corresponding to position 103 in SEQ ID NO: 31;
  h) an A genotype in the heterozygous or homozygous state for SNP marker 8 at a position corresponding to position 115 in SEQ ID NO: 36;
  i) an A genotype in the heterozygous or homozygous state for SNP marker 9 at a position corresponding to position 87 in SEQ ID NO: 41; and/or
  j) a C genotype in the heterozygous or homozygous state for SNP marker 10 at a position corresponding to position 196 in SEQ ID NO: 46.

The present invention discloses a kit for the detection of the rind-turning trait in a melon plant, particularly a cultivated melon plant, wherein said kit comprises at least one PCR oligonucleotide primer pair and probe, selected from:
  a) forward primer of SEQ ID NO: 2 and reverse primer of SEQ ID NO: 5, and probe of SEQ ID NO: 3 for SNP marker 1;
  b) forward primer of SEQ ID NO: 7 and reverse primer of SEQ ID NO: 10, and probe of SEQ ID NO: 8 for SNP marker 2;
  c) forward primer of SEQ ID NO: 12 and reverse primer of SEQ ID NO: 15, and probe of SEQ ID NO: 13 for SNP marker 3;
  d) forward primer of SEQ ID NO: 17 and reverse primer of SEQ ID NO: 20, and probe of SEQ ID NO: 18 for SNP marker 4;
  e) forward primer of SEQ ID NO: 22 and reverse primer of SEQ ID NO: 25, and probe of SEQ ID NO: 23 for SNP marker 5;
  f) forward primer of SEQ ID NO: 27 and reverse primer of SEQ ID NO: 30, and probe of SEQ ID NO: 28 for SNP marker 6;
  g) forward primer of SEQ ID NO: 32 and reverse primer of SEQ ID NO: 35, and probe of SEQ ID NO: 33 for SNP marker 7;
  h) forward primer of SEQ ID NO: 37 and reverse primer of SEQ ID NO: 40, and probe of SEQ ID NO: 38 for SNP marker 8;
  i) forward primer of SEQ ID NO: 42 and reverse primer of SEQ ID NO: 45, and probe of SEQ ID NO: 43 for SNP marker 9;
  j) forward primer of SEQ ID NO: 47 and reverse primer of SEQ ID NO: 50, and probe of SEQ ID NO: 48 for SNP marker 10.

The present invention also discloses the use of at least one, at least two or at least three of the SNP markers according to the invention for diagnostic selection and/or genotyping of the rind-turning trait locus in a melon plant, particularly a cultivated melon plant The present invention further discloses the use of at least one, at least two or at least three of the SNP markers according to the invention for identifying in a melon plant, particularly a cultivated melon plant, more particularly a melon plant according to the invention, the presence of the genotype associated with the rind-turning trait and/or for monitoring the introgression of the rind-turning trait in a melon plant, particularly a cultivated melon plant, particularly a melon plant comprising a LSL10 allele.

The invention further discloses a polynucleotide (amplification product) obtainable in a PCR reaction involving at least one oligonucleotide primer or a pair of PCR oligonucleotide primers selected from Table 4, which amplification product corresponds to an amplification product obtainable from melon line 19MNA106815, representative seed of which is deposited under ATCC Accession No. PTA-126875, or a progeny or an ancestor thereof, comprising the rind-turning introgressed sequence of the invention.

Also contemplated herein is a polynucleotide that has at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the rind-turning trait locus.

The present invention therefore further relates in one embodiment to derived markers, particularly to derived primers or probes, developed from an amplification product according to the invention and as described herein above by methods known in the art, which derived markers are genetically linked to the rind-turning trait locus.

Methods of Breeding.

In a further embodiment, the invention provides a method for producing a cultivated melon plant, preferably a cultivated Cantaloupe melon plant, more preferably a *Cucumis melo* var. *cantalupensis* plant or a *Cucumis melo* var. *reticulatus* plant, wherein said plant produces melon fruits exhibiting a long shelf-life phenotype as well as a rind-turning phenotype when reaching full maturity, wherein the method comprising the steps of
 a) crossing a plant according to any one of the preceding embodiments with a cultivated melon plant lacking said LSL10 allele and said introgressed sequence;
 b) selecting a progeny plant comprising at least one copy of an LSL10 allele and at least one copy of an introgressed sequence from *C. melo* var. *dudaim* located on chromosome 6, said selecting step comprising detecting at least one of the following SNP markers:
  i) an A genotype in the heterozygous or homozygous state for SNP marker 1 at a position corresponding to position 61 in SEQ ID NO: 1;
  ii) a G genotype in the heterozygous or homozygous state for SNP marker 2 at a position corresponding to position 55 in SEQ ID NO: 6;
  iii) a G genotype in the heterozygous or homozygous state for SNP marker 3 at a position corresponding to position 65 in SEQ ID NO: 11;
  iv) a G genotype in the heterozygous or homozygous state for SNP marker 4 at a position corresponding to position 49 in SEQ ID NO: 16;
  v) a C genotype in the heterozygous or homozygous state for SNP marker 5 at a position corresponding to position 53 in SEQ ID NO: 21;
  vi) a G genotype in the heterozygous or homozygous state for SNP marker 6 at a position corresponding to position 83 in SEQ ID NO: 26;
  vii) a G genotype in the heterozygous or homozygous state for SNP marker 7 at a position corresponding to position 103 in SEQ ID NO: 31;
  viii) an A genotype in the heterozygous or homozygous state for SNP marker 8 at a position corresponding to position 115 in SEQ ID NO: 36;
  ix) an A genotype in the heterozygous or homozygous state for SNP marker 9 at a position corresponding to position 87 in SEQ ID NO: 41; and/or
  x) a C genotype in the heterozygous or homozygous state for SNP marker 10 at a position corresponding to position 196 in SEQ ID NO: 46;
thereby producing a plant producing fruits with a long shelf-life phenotype as well as a rind-turning phenotype when reaching full maturity.

In a further embodiment, the invention provides a method for producing a cultivated melon plant, preferably a cultivated Cantaloupe melon plant, more preferably a *Cucumis melo* var. *cantalupensis* plant or a *Cucumis melo* var. *reticulatus* plant, wherein said plant produces melon fruits exhibiting a long shelf-life phenotype as well as a rind-turning phenotype when reaching full maturity, wherein the method comprising the steps of
 a) crossing a plant according to any one of the preceding embodiments with a cultivated melon plant comprising at least one copy of an LSL10 allele but lacking an introgressed sequence associated with the rind-turning phenotype;
 b) selecting a progeny plant comprising at least one copy of an introgressed sequence from *C. melo* var. *dudaim* located on chromosome 6, said selecting step comprising detecting the favourable genotype for at least one of the following SNP markers:
  i) an A genotype in the heterozygous or homozygous state for SNP marker 1 at a position corresponding to position 61 in SEQ ID NO: 1;
  ii) a G genotype in the heterozygous or homozygous state for SNP marker 2 at a position corresponding to position 55 in SEQ ID NO: 6;
  iii) a G genotype in the heterozygous or homozygous state for SNP marker 3 at a position corresponding to position 65 in SEQ ID NO: 11;
  iv) a G genotype in the heterozygous or homozygous state for SNP marker 4 at a position corresponding to position 49 in SEQ ID NO: 16;
  v) a C genotype in the heterozygous or homozygous state for SNP marker 5 at a position corresponding to position 53 in SEQ ID NO: 21;
  vi) a G genotype in the heterozygous or homozygous state for SNP marker 6 at a position corresponding to position 83 in SEQ ID NO: 26;
  vii) a G genotype in the heterozygous or homozygous state for SNP marker 7 at a position corresponding to position 103 in SEQ ID NO: 31;
  viii) an A genotype in the heterozygous or homozygous state for SNP marker 8 at a position corresponding to position 115 in SEQ ID NO: 36;
  ix) an A genotype in the heterozygous or homozygous state for SNP marker 9 at a position corresponding to position 87 in SEQ ID NO: 41; and/or
  x) a C genotype in the heterozygous or homozygous state for SNP marker 10 at a position corresponding to position 196 in SEQ ID NO: 46;
thereby producing a plant producing fruits with a long shelf-life phenotype as well as a rind-turning phenotype when reaching full maturity.

In a further embodiment, the invention relates to the method of any of the preceding embodiments, wherein the method further comprises:
 c) selfing the selected progeny or crossing the selected progeny with another melon plant to produce further progeny.

In a further embodiment, the invention relates to the method of the preceding embodiment, wherein further progeny is selected and selfed/crossed for 2 to 10 more generations.

In a further embodiment, the invention relates to the method of any of the preceding embodiments, wherein the plant of step a) is melon line 19MNA106815, representative seed of which is deposited under ATCC Accession No. PTA-126875, or a progeny or an ancestor thereof.

In another embodiment the invention relates to a method of providing a rind-turning melon plant, plant part or seed, wherein said method comprises the following steps:
 a) Crossing a 1$^{st}$ plant lacking the rind-turning introgressed sequence of the invention with a 2$^{nd}$ melon plant according to any one of previous embodiments, b) Obtaining a progeny melon plant, and,
c) Optionally, selecting a plant of said progeny characterized in that said plant exhibits rind-turning phenotype.

In a further embodiment the invention relates to the method of the preceding embodiment wherein the 1st melon plant is a plant already comprising at least one copy of an LSL10 allele. In a further embodiment the invention relates to the method of the preceding embodiment wherein the $2^{nd}$ melon plant is melon line 19MNA106815, representative seed of which is deposited under ATCC Accession No. PTA-126875, or a progeny or an ancestor thereof.

In another embodiment the invention relates to a method for producing a rind-turning melon plant comprising the following steps:
a) Providing seeds of a melon plant according to any of the preceding embodiments,
b) Germinating said seed and growing a mature, fertile plant therefrom,
c) Inducing self-pollination of said plant under a), growing fruits and harvesting the fertile seeds therefrom, and
d) Growing plants from the seeds harvested under c) and selecting rind-turning melon plant.

In another embodiment the invention relates to a method for providing a rind-turning phenotype to a melon plant, comprising the steps of:
a) selecting a melon, which comprises a rind-turning trait associated with one introgressed sequence located on chromosome 6, wherein said trait can be identified by the presence of at least one of the SNP markers listed in Table 4;
b) crossing said plant of step a), which comprises a rind-turning trait, with a melon plant, particularly a cultivated melon plant, which does not comprise a rind-turning trait and does not show a rind-turning phenotype, as compared to the plant of step a), and
c) selecting progeny from said cross which shows rind-turning phenotype, as compared to the plant of step b).

In a further embodiment the invention relates to the method of the preceding embodiment wherein the recipient plant of step b) comprises at least one copy of an LSL10 allele.

In a further embodiment, the invention relates to a method for producing a F1 melon plant exhibiting a rind-turning phenotype, the method comprising crossing an inbred melon plant, which is a plant according to any one of the preceding embodiments, with a different inbred melon plant to produce F1 hybrid progeny.

Methods of Selection.

In a further embodiment, the invention provides a method for identifying a cultivated melon plant, preferably a cultivated Cantaloupe melon plant, more preferably a *Cucumis melo* var. *reticulatus* plant or a *Cucumis melo* var. *cantalupensis* plant, wherein said plant produces melon fruits exhibiting a long shelf life phenotype as well as a rind-turning phenotype when reaching full maturity, wherein said plant comprises at least one copy of an LSL10 allele and at least one copy of an introgressed sequence from *C. melo* var. *dudaim* located on chromosome 6, wherein said method comprising the step of detecting at least one of the following SNP markers:
a) an A genotype in the heterozygous or homozygous state for SNP marker 1 at a position corresponding to position 61 in SEQ ID NO: 1;
b) a G genotype in the heterozygous or homozygous state for SNP marker 2 at a position corresponding to position 55 in SEQ ID NO: 6;
c) a G genotype in the heterozygous or homozygous state for SNP marker 3 at a position corresponding to position 65 in SEQ ID NO: 11;
d) a G genotype in the heterozygous or homozygous state for SNP marker 4 at a position corresponding to position 49 in SEQ ID NO: 16;
e) a C genotype in the heterozygous or homozygous state for SNP marker 5 at a position corresponding to position 53 in SEQ ID NO: 21;
f) a G genotype in the heterozygous or homozygous state for SNP marker 6 at a position corresponding to position 83 in SEQ ID NO: 26;
g) a G genotype in the heterozygous or homozygous state for SNP marker 7 at a position corresponding to position 103 in SEQ ID NO: 31;
h) an A genotype in the heterozygous or homozygous state for SNP marker 8 at a position corresponding to position 115 in SEQ ID NO: 36;
i) an A genotype in the heterozygous or homozygous state for SNP marker 9 at a position corresponding to position 87 in SEQ ID NO: 41; and/or
j) a C genotype in the heterozygous or homozygous state for SNP marker 10 at a position corresponding to position 196 in SEQ ID NO: 46;
thereby identifying a melon plant producing fruits with a long shelf-life phenotype as well as a rind-turning phenotype when reaching full maturity.

In a further embodiment, the invention relates to the method of the preceding embodiment, wherein the method further comprises the step of detecting the following SNP marker
a) a G genotype in the heterozygous or homozygous state for SNP marker 11 at a position corresponding to position 107 in SEQ ID NO: 51.

In a further embodiment, the invention relates to the method of any of the preceding embodiments, wherein said method further comprises selecting a melon plant comprising the favourable genotype at said one or more SNP markers, and crossing the selected melon plant with a second melon plant to produce progeny melon plants that comprise at least one favourable genotype at said SNP markers and exhibits the rind-turning phenotype of the invention.

In another embodiment the invention relates to a method of identifying a melon plant comprising the rind-turning introgressed sequence of the invention, wherein said method comprises the steps of:
a) providing a population segregating for the rind-turning trait,
b) screening the segregating population for a member exhibiting rind-turning phenotype, wherein said trait can be identified by the presence of the rind-turning introgressed sequence of the invention,
c) selecting one member of the segregating population, wherein said member comprises the rind-turning trait.

In a further embodiment, the invention provides a method for identifying a cultivated melon plant comprising an introgressed sequence on chromosome 6, wherein said introgressed sequence confers rind-turning phenotype, comprising:
a) providing a population segregating for rind-turning phenotype,
b) screening said population using a kit which detects at least one of the SNP markers listed in Table 4, and, c) identifying a plant comprising said at least one SNP marker selected in the list of Table 4.

In a further embodiment, the invention provides a method for identifying further melon source of rind-turning trait on chromosome 6, comprising:
a) providing a melon plant or a melon accession or a plurality of melon plants or accessions,
b) screening said melon plant or a melon accession or a plurality of melon plants or accessions using a kit which detects at least one of the SNP markers listed in Table 4, and,
c) identifying a melon plant or accession comprising said at least one SNP marker selected in the list of Table 4.

In yet another embodiment, the invention relates to the use of a SNP marker amplified from the genome of a melon plant according to any of the preceding embodiments, preferably from the genome of melon line 19MNA106815, representative seed of which is deposited under ATCC Accession No. PTA-126875, or a progeny or an ancestor thereof, wherein said SNP marker is identified using one of the following kits:
a) forward primer of SEQ ID NO: 2 and reverse primer of SEQ ID NO: 5, and probe of SEQ ID NO: 3;
b) forward primer of SEQ ID NO: 7 and reverse primer of SEQ ID NO: 10, and probe of SEQ ID NO: 8;
c) forward primer of SEQ ID NO: 12 and reverse primer of SEQ ID NO: 15, and probe of SEQ ID NO: 13;
d) forward primer of SEQ ID NO: 17 and reverse primer of SEQ ID NO: 20, and probe of SEQ ID NO: 18;
e) forward primer of SEQ ID NO: 22 and reverse primer of SEQ ID NO: 25, and probe of SEQ ID NO: 23;
f) forward primer of SEQ ID NO: 27 and reverse primer of SEQ ID NO: 30, and probe of SEQ ID NO: 28;
g) forward primer of SEQ ID NO: 32 and reverse primer of SEQ ID NO: 35, and probe of SEQ ID NO: 33;
h) forward primer of SEQ ID NO: 37 and reverse primer of SEQ ID NO: 40, and probe of SEQ ID NO: 38;
i) forward primer of SEQ ID NO: 42 and reverse primer of SEQ ID NO: 45, and probe of SEQ ID NO: 43; and/or
j) forward primer of SEQ ID NO: 47 and reverse primer of SEQ ID NO: 50, and probe of SEQ ID NO: 48;
and wherein said SNP marker is indicative of the presence of the rind-turning trait in a melon plant, to identify a melon plant that comprises and exhibits the rind-turning trait.

In a further embodiment, the invention relates to a method for assessing the genotype of a cultivated melon plant, preferably a cultivated *Cucumis melo* plant, more preferably a *Cucumis melo* var. *reticulatus* plant or a *Cucumis melo* var. *cantalupensis* plant, exhibiting rind-turning phenotype, said method comprising the steps of:
a) providing a sample from said plant, and,
b) detecting in said sample a QTL locus located on chromosome 6 and associated with said rind-turning phenotype, said QTL locus being flanked by SNP markers 1 and 10, and at least one of the following SNP markers:
i) an A genotype in the heterozygous or homozygous state for SNP marker 1 at a position corresponding to position 61 in SEQ ID NO: 1;
ii) a G genotype in the heterozygous or homozygous state for SNP marker 2 at a position corresponding to position 55 in SEQ ID NO: 6;
iii) a G genotype in the heterozygous or homozygous state for SNP marker 3 at a position corresponding to position 65 in SEQ ID NO: 11;
iv) a G genotype in the heterozygous or homozygous state for SNP marker 4 at a position corresponding to position 49 in SEQ ID NO: 16;
v) a C genotype in the heterozygous or homozygous state for SNP marker 5 at a position corresponding to position 53 in SEQ ID NO: 21;
vi) a G genotype in the heterozygous or homozygous state for SNP marker 6 at a position corresponding to position 83 in SEQ ID NO: 26;
vii) a G genotype in the heterozygous or homozygous state for SNP marker 7 at a position corresponding to position 103 in SEQ ID NO: 31;
viii) an A genotype in the heterozygous or homozygous state for SNP marker 8 at a position corresponding to position 115 in SEQ ID NO: 36;
ix) an A genotype in the heterozygous or homozygous state for SNP marker 9 at a position corresponding to position 87 in SEQ ID NO: 41; and/or
x) a C genotype in the heterozygous or homozygous state for SNP marker 10 at a position corresponding to position 196 in SEQ ID NO: 46; and/or
xi) any other DNA marker associated with said QTL locus flanked by SNP markers 1 and 10.

In a further embodiment, the invention relates to a method of identifying in a cultivated melon plant, preferably a cultivated *Cucumis melo* plant, more preferably a *Cucumis melo* var. *reticulatus* plant or a *Cucumis melo* var. *cantalupensis* plant, an introgressed sequence associated with rind-turning phenotype, said method comprising the step of detecting in said plant an allele of at least one DNA marker that is genetically linked to a QTL locus associated with said rind-turning phenotype, wherein said allele maps within 10 cM, preferably within 5 cM of said QTL locus located on chromosome 6 in a genomic region flanked by SNP markers 1 and 10.

In an alternative embodiment, the invention relates to a method of identifying in a cultivated melon plant, preferably a cultivated *Cucumis melo* plant, more preferably a *Cucumis melo* var. *reticulatus* plant or a *Cucumis melo* var. *cantalupensis* plant, an introgressed sequence associated with rind-turning phenotype, said method comprising the step of detecting in said plant an allele of at least one DNA marker that is genetically linked to a QTL locus associated with said rind-turning phenotype, wherein said allele maps between position 25115792 bp in the public reference genome v CM3.5.1 and position 30769753 bp in the public reference genome v CM3.5.1 on said QTL locus located on chromosome 6 in a genomic region flanked by SNP markers 1 and 10.

In a further embodiment, the invention relates to the method of the preceding embodiments, wherein said QTL locus can be identified by at least one of the following SNP markers
a) an A genotype in the heterozygous or homozygous state for SNP marker 1 at a position corresponding to position 61 in SEQ ID NO: 1;
b) a G genotype in the heterozygous or homozygous state for SNP marker 2 at a position corresponding to position 55 in SEQ ID NO: 6;
c) a G genotype in the heterozygous or homozygous state for SNP marker 3 at a position corresponding to position 65 in SEQ ID NO: 11;
d) a G genotype in the heterozygous or homozygous state for SNP marker 4 at a position corresponding to position 49 in SEQ ID NO: 16;

e) a C genotype in the heterozygous or homozygous state for SNP marker 5 at a position corresponding to position 53 in SEQ ID NO: 21;

f) a G genotype in the heterozygous or homozygous state for SNP marker 6 at a position corresponding to position 83 in SEQ ID NO: 26;

g) a G genotype in the heterozygous or homozygous state for SNP marker 7 at a position corresponding to position 103 in SEQ ID NO: 31;

h) an A genotype in the heterozygous or homozygous state for SNP marker 8 at a position corresponding to position 115 in SEQ ID NO: 36;

i) an A genotype in the heterozygous or homozygous state for SNP marker 9 at a position corresponding to position 87 in SEQ ID NO: 41; and/or j) a C genotype in the heterozygous or homozygous state for SNP marker 10 at a position corresponding to position 196 in SEQ ID NO: 46.

In a further embodiment, the invention relates to the method of the preceding embodiment, wherein said method further comprises the step of selecting a cultivated melon plant, preferably a cultivated *Cucumis melo* plant, more preferably a *Cucumis melo* var. *reticulatus* plant or a *Cucumis melo* var. *cantalupensis* plant, comprising said introgressed sequence.

In a further embodiment, the invention relates to the method of the preceding embodiment, wherein said QTL locus can be identified by at least one of the following SNP markers a) an A genotype in the heterozygous or homozygous state for SNP marker 1 at a position corresponding to position 25115792 bp in the public reference genome v CM3.5.1;

b) a G genotype in the heterozygous or homozygous state for SNP marker 2 at a position corresponding to position 25507734 bp in the public reference genome v CM3.5.1;

c) a G genotype in the heterozygous or homozygous state for SNP marker 3 at a position corresponding to position 25660237 bp in the public reference genome v CM3.5.1;

d) a G genotype in the heterozygous or homozygous state for SNP marker 4 at a position corresponding to position 25714720 bp in the public reference genome v CM3.5.1;

e) a C genotype in the heterozygous or homozygous state for SNP marker 5 at a position corresponding to position 26327861 bp in the public reference genome v CM3.5.1;

f) a G genotype in the heterozygous or homozygous state for SNP marker 6 at a position corresponding to position 27206596 bp in the public reference genome v CM3.5.1;

g) a G genotype in the heterozygous or homozygous state for SNP marker 7 at a position corresponding to position 28161883 bp in the public reference genome v CM3.5.1;

h) an A genotype in the heterozygous or homozygous state for SNP marker 8 at a position corresponding to position 29331322 bp in the public reference genome v CM3.5.1;

i) an A genotype in the heterozygous or homozygous state for SNP marker 9 at a position corresponding to position 30261023 bp in the public reference genome v CM3.5.1; and/or j) a C genotype in the heterozygous or homozygous state for SNP marker 10 at a position corresponding to position 30769753 bp in the public reference genome v CM3.5.1.

In a further embodiment, the invention relates to the method of the preceding embodiment, wherein said method further comprises the step of selecting a cultivated melon plant, preferably a cultivated *Cucumis melo* plant, more preferably a *Cucumis melo* var. *reticulatus* plant or a *Cucumis melo* var. *cantalupensis* plant, comprising said introgressed sequence.

In a further embodiment, the invention relates to a method of identifying a cultivated melon plant, preferably a cultivated *Cucumis melo* plant, more preferably a *Cucumis melo* var. *reticulatus* plant or a *Cucumis melo* var. *cantalupensis* plant, exhibiting rind-turning phenotype by identifying a QTL associated with said rind-turning phenotype, the method comprising the steps of:

a) detecting at least one DNA marker from a melon plant, which DNA marker is linked to a chromosomal interval associated with rind-turning phenotype, wherein said chromosomal interval is flanked on each side by SNP markers having at least 80% sequence identity to SEQ ID NOs: 1 and 46; and b) identifying said melon plant comprising said at least one DNA marker.

Methods of Cultivation and Uses.

The present invention also relates to a method for reducing fruit consumption waste during cultivation of melon plant and harvest of melon fruit, the method comprising the steps of:

a) sowing a melon field with seeds growing into a melon plant according to any of the preceding embodiments;

b) monitoring the rind colour turn from green when immature into yellow when reaching full maturity, preferably using an assay as described in Example 2 below;

c) harvesting the fruits at full maturity for which the rind colour ranges from 15 to 20 (A-D) when measured using the colour patch of the Royal Horticultural Society Colour Chart.

The plants of this invention when used in such method allows for the best harvest timing point, when the melon fruits have reached full maturity. Consequently, melon fruits arrive on the markets at their optimal consumption state, thereby limiting fruit waste observed with non-matured or over-matured melon fruits.

The present invention further relates to the use of rind-turning propagating material obtainable from a melon plant according to any of the preceding embodiments for growing a melon plant in order to produce rind-turning melon plants wherein said rind-turning phenotype may be assessed in a standard assay, particularly an assay as described in Example 2 below.

The present invention also relates to the use of rind-turning propagating material obtainable from a melon plant according to any of the preceding embodiments for producing melon fruits.

In another embodiment the invention relates to the use a cultivated melon plant, plant part or seed, more preferably a cultivated *Cucumis melo* plant, more preferably a *Cucumis melo* var. *reticulatus* plant or a *Cucumis melo* var. *cantalupensis* plant, plant part or seed according to any of the preceding embodiments for growing a plant and producing and harvesting crops and/or fruits.

In another embodiment the invention relates to the use of a cultivated melon plant, more preferably a cultivated *Cucu-*

*mis melo* plant, more preferably a *Cucumis melo* var. *reticulatus* plant or a *Cucumis melo* var. *cantalupensis* plant, according to any of the preceding embodiments for producing fruits for the fresh market or for food processing.

In another embodiment the invention relates to the use of a cultivated melon plant, plant part or seed, preferably a cultivated *Cucumis melo* plant, more preferably a *Cucumis melo* var. *reticulatus* plant or a *Cucumis melo* var. *cantalupensis* plant, plant part or seed according to any of preceding embodiments, wherein said cultivated melon plant, plant part or seed, preferably the cultivated *Cucumis melo* plant, plant part or seed is of melon line 19MNA106815, representative seed of which is deposited under ATCC Accession No. PTA-126875, or a progeny or an ancestor thereof.

In a further embodiment the invention relates to the use of a cultivated melon plant, plant part or seed, more preferably a cultivated *Cucumis melo* plant, more preferably a *Cucumis melo* var. *reticulatus* plant or a *Cucumis melo* var. *cantalupensis* plant, plant part or seed according to any of the preceding embodiments to sow a field, a greenhouse, or a plastic house.

In another embodiment the invention relates to the use of a cultivated melon plant, more preferably a cultivated *Cucumis melo* plant, more preferably a *Cucumis melo* var. *reticulatus* plant or a *Cucumis melo* var. *cantalupensis* plant, according to any of the preceding embodiments to optimize the harvesting time of melon fruits by visual monitoring of the fruit rind colour, indicative of the full maturity of the fruits.

In a further embodiment the invention relates to the use of a melon plant according to any of the preceding embodiments to confer the rind-turning trait to a melon plant lacking said trait. The invention further relates to the use of a melon plant according to any of the preceding embodiments to introgress a rind-turning trait into a melon plant lacking said trait.

In a further embodiment the invention relates to the use of any of SEQ ID NOs 1-50 for screening a population of melon plants for the presence of a QTL locus located on chromosome 6 and associated with a rind-turning phenotype.

In a further embodiment the invention relates to the use of any of SEQ ID NOs 1, 6, 11, 16, 21, 26, 31, 36, 41 or 46 for screening a population of melon plants for the presence of a QTL locus located on chromosome 6 and associated with a rind-turning phenotype.

Based on the description of the present invention, the skilled person who is in possession of melon line 19MNA106815, representative seed of which is deposited under ATCC Accession No. PTA-126875, or a progeny or an ancestor thereof, comprising said introgressed genetic sequence as well as at least one copy of an LSL10 allele, as described herein, has no difficulty to transfer said introgressed genetic sequence of the present invention to other melon plants of various types using breeding techniques well-known in the art with the support of SNP markers herein disclosed.

Seed Deposit Details

Applicant has made a deposit of at least 625 seeds of *Cucumis melo* var. *reticulatus* hybrid plant 19MNA106815 with ATCC (American Type Culture Collection (ATCC), 10801 University Boulevard, Manassas, VA 20110 USA) on 19 Oct. 2020 under ATCC Accession No. PTA-126875.

Applicant elects for the expert solution and requests that the deposited material be released only to an Expert according to Rule 32(1) EPC or corresponding laws and rules of other countries or treaties (Expert Witness clause), until the mention of the grant of the patent publishes, or from 20 years from the date of filing if the application is refused, withdrawn, or deemed to be withdrawn.

*Cucumis melo* var. *reticulatus* hybrid plant 19MNA106815 is heterozygous for the LSL10 allele as well as the rind-turning QTL on chromosome 6, i.e., line 19MNA106815 comprises one copy of an LSL10 allele and one copy of an introgressed sequence from *C. melo* var. *dudaim* located on chromosome 6 and associated with the rind-turning phenotype.

EXAMPLES

Example 1: Germplasm and Population Development

Example 1A. Donor Development

A cross between a *Cucumis melo* var. *dudaim* plant (turning at maturity) was made with a *Cucumis melo* var. *reticulatus* ("09MSP006888") plant (non-turning at maturity) to obtain F1 plants identified as "10MSP002234". The F1 plants were selfed to produce F2 population referred to herein as "12MSP005549". 200 F2 plants were sown and advanced to F3 families using single seed descent method. F3 families were evaluated by phenotypic evaluation for rind-turning trait in the field in California. Best F3 family referred to herein as "13MSP005602" was advanced to F4 generation using self-pollination. Best F4 progeny was selected based on best and stable expression of the trait. Rind-turning trait was measured with the Royal Horticultural Society Colour Chart and phenotypic expression of the rind-turning trait corresponds to a 15-20 (A-D) colour range on the Colour Chart. One F4 line was found to be stable for the trait and was designated as "14MNA106599". This *Cucumis melo* var. *reticulatus* line was used as a donor to convert elite parental lines with rind-turning trait.

Example 1B. Population Development for Genetic Mapping the Rind-Turning Trait

A F2 mapping population was developed using a *Cucumis melo* var. *reticulatus* F3 line designated "13MSP005602" (see Example 1A) and a *Cucumis melo* var. *cantaloupensis* long shelf life, LSL10, inbred line. The F2 population was designated as "14CME-BWS3". 800 F2 individual plants were sown in the field in California and phenotypic evaluation was done for the expression of the rind-turning trait in a long shelf life LSL10 background.

Example 2: Protocols

Example 2A. Evaluation and Scoring of Rind-Turning Trait Phenotype

In a normal long shelf life, LSL10, melon background, the rind of a fully matured fruit remains greyish green to green. This corresponds to color range of 135-143 (A-D) when using the Royal Horticultural Society Color Chart (Cuevas et al., 2010). Fruits were monitored for maturity based on color change from green to yellow in long shelf life, LSL10, melon plants comprising at least one copy of QTL6. In the latter plants, fruit colour turns to yellow upon maturity, the yellow colour range corresponding to 15-20 (A-D) using the Royal Horticultural Society Color Chart. Days to reach full maturity (and to observe the associated rind color change)

typically varied from 82 to 85 days based on normal daily environmental conditions in California summer season.

Example 2B. Evaluation of the Long Shelf-Life Phenotype

Cantaloupe long shelf life, LSL10, melons comprising at least one copy of QTL6 were evaluated for their ability to produce fruits having retained their long shelf-life characteristics upon maturity. At maturity, there is no formation of abscission layer at peduncle attachment hence fruit do not slip from the vine.

Example 2C. Method of Identifying the QTL and Corresponding Introgressed Sequence Underlying the Rind-Turning Trait For QTL discovery, the 800 F2 individuals of the "14CME-BWS3" population were pre-screened with the LSL10 allele marker (see Example 6), and 372 F2 individuals containing at least one copy of the LSL10 locus were selected and genotyped with 150 genetic markers spanning the genome at regular intervals. A genetic map was constructed and rind-turning phenotypic data of the 372 selected individuals used for QTL detection.

The QTL detection was performed using the R/qtl package in the R statistical framework. First, the function 'calc.genoprob' was used to calculate the genotype probabilities (step 1 cM). Haley-Knott regression was performed to provide an approximation of the results of standard interval mapping. Then, the function 'stepwiseqtl' was invoked, which provides a fully automated model selection forward/backward algorithm. LOD threshold for main effect was determine by 10,000 permutations. This algorithm considers different possible interactions (e.g., epistasis). The function 'refineqtl' was used to refine the locations of QTL in the context of a multiple QTL model (maximum likelihood estimates). The function 'fitqtl' was used to fit a defined QTL model and obtain estimates of QTL effects.

Example 3: Identification of One QTL Associated with Rind-Turning Phenotype

Example 3A. Effect of the QTL Located on Chromosome 6 on the Rind-Turning at Maturity One QTL was identified based on the rind-turning phenotypes of the 372 selected F2 individuals from the "14CME-BWS3" population. Table 1 shows the chromosomal location, the effect of the QTL measured as LOD score, and the percentage of variation explained by the QTL on chromosome 6 for rind-turning phenotype.

TABLE 1

Significant QTL associated with rind-turning phenotype.

| Chromosome | LOD | % var | Pvalue (Chi2) |
|---|---|---|---|
| 6 | 25.85 | 23.9 | <0.001 |

"LOD" = log likelihood score, "% var" = percent phenotypic variation explained by the QTL, "Pvalue (Chi2)" = the probability of the QTL detected due to random chance by chi-square analysis.

The QTL showed an additive or semi-dominant effect in the "14CME-BWS3" discovery population. The presence of only one copy of the donor allele at the QTL location was showing an intermediate rind-turning phenotype compared to when two homozygous parental alleles are present.

Example 4: Introgression of the Rind-Turning Conferring Sequence into a LSL10 Cantaloupe Background The *Cucumis melo* var. *reticulatus* LSL10 cantaloupe background is non-turning at maturity whereas *Cucumis melo* var. *dudaim* melon fruit rind changes color on maturity. The genetic sequence associated with rind-turning phenotype present in *Cucumis melo* var. *dudaim* melon plants was introgressed into LSL10 cantaloupe breeding material by selecting plants as described in Example 2 and backcrossing them to LSL10 cantaloupe breeding lines.

The advanced breeding lines highlighted a similar phenotype to that of the recurrent parent in terms of long shelf life and non-slip characteristics while comprising the favourable introgressed sequence for rind-turning phenotype. The phenotyping results, along with the results of testing for the presence or absence of representative markers in QTL6 and LSL10 allele, are summarized in Table 2 below.

TABLE 2

Presence or absence of characterizing SNP markers for QTL6 and LSL10, and corresponding phenotypes.

| | Material | | | |
|---|---|---|---|---|
| | Rind | QTL6 markers | | LSL10 marker |
| ID and type | colour at maturity | SE4033 SNP3 | SE4009 SNP6 | SE3729 SNP9 | SE1787 SNP11 |
| 1. 14MNA106599/Donor (F4) | 19A | 1* | 1 | 1 | 0 |
| 2. 19MNA106815/Seed Deposit (F1) | 19A | H | H | H | H |
| 3. 15MNA888079/Recurrent Parent 1 | 138C | 0 | 0 | 0 | 1 |
| 4. 15MNA888070/Recurrent Parent 2 | 139A | 0 | 0 | 0 | 1 |
| 5. 20ALL111SGD_MM/Converted RP2 | 19B | 1 | 1 | 1 | 1 |
| 6. 20ALL111SGE_MM/Converted RP2 | 19B | 1 | 1 | 1 | 1 |
| 7. 20ALL111SMC_MM/Converted RP2 | 19B | 1 | 1 | 1 | 1 |

TABLE 2-continued

Presence or absence of characterizing SNP markers for QTL6 and LSL10, and corresponding phenotypes.

| | | Material | | | |
|---|---|---|---|---|---|
| | | | QTL6 markers | | LSL10 marker |
| | Rind | | | | |
| ID and type | colour at maturity | SE4033 SNP3 | SE4009 SNP6 | SE3729 SNP9 | SE1787 SNP11 |
| 8. 20ALL111SME_MM/Converted RP2 | 19B | 1 | 1 | 1 | 1 |
| 9. 20ALL111SMG_MM/Converted RP1 | 19A | 1 | 1 | 1 | 1 |
| 10. 20ALL111SMI_MM/Converted RP1 | 19A | 1 | 1 | 1 | 1 |
| 11. MS0550/Experimental hybrid (F1) | 19A | H | H | H | H |
| 12. MS0539/Experimental hybrid (F1) | 19A | H | H | H | H |
| 13. Sweet Spring/Commercial hybrid | 138C | 0 | 0 | 0 | H |

*"1" indicates homozygous; "H" indicates heterozygous; and "0" indicates not present Existing commercial hybrid (Sweet Spring) as well as the recurrent LSL10 cantaloupe recurrent parent (materials 3 and 4) are non-climacteric, non-slip, and non-rind-turning. They only bear at least one copy of the LSL10 allele and their melon fruit rind colour stays green upon maturity (RHS range 135 to 143 (A-D)). On the contrary, all converted cantaloupe melon lines comprising the QTL6 as well as the LSL10 allele (materials 5 to 10) exhibit a rind-turning phenotype (RHS range 15 to 20 (A-D)) while retaining the long shelf life and non-slip characteristics of the matured melon fruit. Furthermore, experimental hybrids, including the deposited material (materials 2, 11 and 12), are also exhibiting rind-turning phenotype (RHS range 15 to 20 (A-D)) even though they comprise only one copy of QTL6. That is, all lines and hybrids comprising at least one copy of QTL6, characterized by SNP markers spanning genetic interval 64.8-73.7 cM, and at least one copy of the LSL10 SNP marker, exhibit a rind-turning phenotype while preserving the long shelf life and non-slip characteristics of the melon fruit.

Within this region, ten SNPs, SE3980, SE3992, SE4033, SE4031, SE3981, SE4009, SE3978, SE3987, SE3729 and SE3982 within the QTL interval showed specificity for the selection of donor rind-turning allele, and from them, SNP markers SE4033, SE4031, SE3981, SE4009, SE3978, SE3987, SE3729, were the most closely linked to the QTL. Table 3 below shows both genetic and physical positions of the QTL6 as well as the positions of the ten SNP markers tightly linked with said rind-turning (RT) QTL allele.

TABLE 3

Genetic map of the QTL on chromosome 6

| SNP ID | SNP Locus | Position (cM) | Physical position PIT92 v7 (bp) | Physical position Public v CM3.5.1 (bp) | Observation |
|---|---|---|---|---|---|
| 1 | SE3980 | 64.8 | 24564648 | 25115792 | SNP specific to RT allele |
| 2 | SE3992 | 65.6 | 24956590 | 25507734 | SNP specific to RT allele |
| 3 | SE4033 | 65.9 | 25109093 | 25660237 | SNP specific to RT allele |
| 4 | SE4031 | 66 | 25163576 | 25714720 | SNP specific to RT allele |
| 5 | SE3981 | 67 | 25776717 | 26327861 | SNP specific to RT allele |
| 6 | SE4009 | 68.2 | 26655452 | 27206596 | SNP specific to RT allele |
| 7 | SE3978 | 69.9 | 27610739 | 28161883 | SNP specific to RT allele |
| 8 | SE3987 | 71.5 | 28781178 | 29331322 | SNP specific to RT allele |
| 9 | SE3729 | 72.8 | 29710879 | 30261023 | SNP specific to RT allele |
| 10 | SE3982 | 73.7 | 30220609 | 30769753 | SNP specific to RT allele |

Example 5: Sequence and SNP Marker Information for QTL6

The sequence information of SNP markers SE3980, SE3992, SE4033, SE4031, SE3981, SE4009, SE3978, SE3987, SE3729 and SE3982, and their respective PCR primers/probes for detection is summarized in Table 4 below.

TABLE 4

| MARKER | 1/SE3980 | 2/SE3992 | 3/SE4033 | 4/SE4031 | 5/SE3981 | 6/SE4009 |
|---|---|---|---|---|---|---|
| Donor (*dudaim*) Allele | A | G | G | G | C | G |
| Recipient (*cantalupensis/ reticulatus*) Allele | G | A | A | A | A | A |

TABLE 4-continued

| | | | | | | |
|---|---|---|---|---|---|---|
| Target Sequence: SEQ ID NO. | 1 | 6 | 11 | 16 | 21 | 26 |
| SNP Position in Target SEQ: nt | 61 | 55 | 65 | 49 | 53 | 83 |
| Forward Primer: SEQ ID NO. | 2 | 7 | 12 | 17 | 22 | 27 |
| Reverse Primer: SEQ ID NO. | 5 | 10 | 15 | 20 | 25 | 30 |
| Probe (Donor): SEQ ID NO. | 3 | 8 | 13 | 18 | 23 | 28 |
| Probe (Recipient): SEQ ID NO. | 4 | 9 | 14 | 19 | 24 | 29 |

| MARKER | 7/SE3978 | 8/SE3987 | 9/SE3729 | 10/SE3982 |
|---|---|---|---|---|
| Donor (*dudaim*) Allele | G | A | A | C |
| Recipient (*cantalupensis/reticulatus*) Allele | C | C | G | G |
| Target Sequence: SEQ ID NO. | 31 | 36 | 41 | 46 |
| SNP Position in Target SEQ: nt | 103 | 115 | 87 | 196 |
| Forward Primer: SEQ ID NO. | 32 | 37 | 42 | 47 |
| Reverse Primer: SEQ ID NO. | 35 | 40 | 45 | 50 |
| Probe (Donor): SEQ ID NO. | 33 | 38 | 43 | 48 |
| Probe (Recipient): SEQ ID NO. | 34 | 39 | 44 | 49 |

As a matter of example, SNP marker 1 (SE3980) at position 24564648 bp/25225792 bp on chromosome 6 (based on reference PIT92 v7 sequence or public genome version CM3.5.1 respectively) is characterized by a particular SNP marker (*dudaim* donor vs. recipient allele) at position 61 of the target sequence of SEQ ID NO:1. Corresponding forward and reverse primers of SEQ ID NOs 2 and 5, and probes specific for the donor or recipient alleles of SEQ ID NOs 3 and 4 are also disclosed.

Example 6: Sequence and SNP Marker Information for LSL10 Allele

The genetic map information as well as the sequence information of the SNP marker SE1787 and its respective PCR primers/probes for detection are summarized in Tables 5 and 6 below. This marker can be used to detect the LSL10 allele when introgressed in a *Cucumis melo* var. *cantalupensis* or *reticulatus* background. It can be sourced from the deposited material 19MNA106815, or from other existing publicly available sources such as PI 420176 (Perpina et al. 2017).

TABLE 5

Genetic map of the LSL10 allele on chromosome 10.

| SNP ID | SNP Locus | Position (cM) | Physical position PIT92 v7 (bp) | Physical position Public v CM3.5.1 | Observation |
|---|---|---|---|---|---|
| 11 | SE1787 | 1.2 | 24353123 | 456347 | SNP specific to LSL10 allele |

TABLE 6

| MARKER | 11/SE1787 |
|---|---|
| Donor (seed deposit) LSL10 Allele | G |
| Recipient (*cantalupensis/reticulatus*) non-LSL10 Allele | T |
| Target Sequence: SEQ ID NO. | 51 |
| SNP Position in Target SEQ: nt | 107 |
| Forward Primer: SEQ ID NO. | 52 |
| Reverse Primer: SEQ ID NO. | 55 |
| Probe (Donor): SEQ ID NO. | 53 |
| Probe (Recipient): SEQ ID NO. | 4 |

BIBLIOGRAPHY

Cuevas et al. (2010), Euphytica 173:129-140.
Pech et al. (2008), Plant Science 175:114-120.
Perpina et al. (2017), HortScience 52(11):1633-1638.
Pitrat et al. (2000), Proc. Cucurbitaceae 2000, Eds N. Katzir & H. S. Pqris, Acta Hort. 510.

The invention claimed is:

1. A cultivated melon plant having a long shelf-life phenotype comprising in its genome:
at least one copy of an introgressed sequence from *Cucumis melo* var. *dudaim* conferring a rind-turning phenotype, located on chromosome 6, mapped between position 25115792 bp in the public reference genome v CM3.5.1 and position 30769753 bp in the public reference genome v CM3.5.1, and comprising the following flanking SNP markers:
 i) SEQ ID NO: 1 comprising an A genotype in the heterozygous or homozygous state for SNP marker 1 at a position corresponding to position 61 in SEQ ID NO: 1; and
 ii) SEQ ID NO: 46 comprising a C genotype in the heterozygous or homozygous state for SNP marker 10 at a position corresponding to position 196 in SEQ ID NO: 46;
wherein said introgressed sequence is comprised in melon line 19MNA106815, representative seed of which is deposited under ATCC Accession No. PTA-126875, or a progeny thereof; and
wherein said cultivated melon plant produces melon fruit exhibiting a long shelf-life phenotype, wherein said long shelf-life phenotype is characterized by fruits that do not form an abscission layer at maturity, wherein said melon fruit further exhibits a rind-turning phenotype when reaching full maturity, and wherein said rind-turning phenotype is characterized by a rind colour turning from green when immature into yellow when reaching full maturity.

2. The plant according to claim 1, wherein said melon fruit rind yellow colour at full maturity ranges from 15A to 20D when measured using the colour patch of the Royal Horticultural Society Colour Chart.

3. The plant according to claim 2, wherein said melon fruit rind yellow colour at full maturity is 19A or 19B when measured using the colour patch of the Royal Horticultural Society Colour Chart.

4. The plant according to claim 1, wherein said immature melon fruit rind green colour ranges from 135A to 143D when measured using the colour patch of the Royal Horticultural Society Colour Chart.

5. The plant according to claim 1, wherein said immature melon fruit rind green colour is 138C, 138D or 139A when measured using the colour patch of the Royal Horticultural Society Colour Chart.

6. The plant according to claim 1, wherein:
i) the A genotype for SNP marker 1 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;
ii) the C genotype for SNP marker 10 can be identified in a PCR by amplification of a nucleic acid fragment with a pair of oligonucleotide primers: forward primer of SEQ ID NO: 47 and reverse primer of SEQ ID NO: 50, and probe of SEQ ID NO: 48.

7. The plant according to claim 1, wherein said plant is homozygous for said introgressed sequence located on chromosome 6.

8. The plant of claim 1, wherein said plant is obtained by crossing melon line 19MNA106815, representative seed of which is deposited under ATCC Accession No. PTA-126875, or a progeny thereof comprising said introgressed sequence as found in melon line 19MNA106815, with a melon plant that does not contain said introgressed sequence.

9. The plant of claim 1 wherein said plant is an inbred, a dihaploid or a hybrid plant.

10. A plant of melon line 19MNA106815, representative seed of which is deposited under ATCC Accession No. PTA-126875.

11. A plant part of the plant according to claim 1, wherein said plant part comprises said at least one copy of an introgressed sequence from *Cucumis melo* var. *dudaim*.

12. A seed that produces the plant according to claim 1.

13. A method for producing an F1 melon plant exhibiting rind-turning phenotype, the method comprising crossing the plant of claim 1 wherein said plant is an inbred melon plant, with a different inbred melon plant to produce F1 hybrid progeny exhibiting the rind-turning phenotype.

14. A method of producing melon seed, the method comprising growing a melon plant from the seed of claim 12 and allowing the plant to produce further melon seed.

15. The cultivated melon plant of claim 1, wherein the cultivated melon plant is a cultivated Cantaloupe melon plant.

16. The cultivated melon plant of claim 15, wherein the cultivated Cantaloupe melon plant is:
a) a *Cucumis melo* var. *reticulatus* plant, or
b) a *Cucumis melo* var. *cantalupensis* plant.

17. The plant according to claim 1, wherein the introgressed sequence further comprises one or more of the following SNP markers:
iii) a G genotype in the heterozygous or homozygous state for SNP marker 2 at a position corresponding to position 55 in SEQ ID NO: 6;
iv) a G genotype in the heterozygous or homozygous state for SNP marker 3 at a position corresponding to position 65 in SEQ ID NO: 11;
v) a G genotype in the heterozygous or homozygous state for SNP marker 4 at a position corresponding to position 49 in SEQ ID NO: 16;
vi) a C genotype in the heterozygous or homozygous state for SNP marker 5 at a position corresponding to position 53 in SEQ ID NO: 21;
vii) a G genotype in the heterozygous or homozygous state for SNP marker 6 at a position corresponding to position 83 in SEQ ID NO: 26;
viii) a G genotype in the heterozygous or homozygous state for SNP marker 7 at a position corresponding to position 103 in SEQ ID NO: 31;
ix) an A genotype in the heterozygous or homozygous state for SNP marker 8 at a position corresponding to position 115 in SEQ ID NO: 36; and/or
x) an A genotype in the heterozygous or homozygous state for SNP marker 9 at a position corresponding to position 87 in SEQ ID NO: 41.

18. The plant according to claim 17, wherein said introgressed sequence comprises at least one of SEQ ID NO: 6, SEQ ID NO: 11, SEQ ID NO: 16, SEQ ID NO: 21, SEQ ID NO: 26, SEQ ID NO: 31, SEQ ID NO: 36, and SEQ ID NO: 41.

19. The plant according to claim 17, wherein:
iii) the G genotype for SNP marker 2 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;
iv) the G genotype for SNP marker 3 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13;
v) the G genotype for SNP marker 4 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18;
vi) the C genotype for SNP marker 5 can be identified in a PCR by amplification of a nucleic acid fragment with a pair of oligonucleotide primers: forward primer of SEQ ID NO: 22 and reverse primer of SEQ ID NO: 25, and probe of SEQ ID NO: 23;
vii) the G genotype for SNP marker 6 can be identified in a PCR by amplification of a nucleic acid fragment with a pair of oligonucleotide primers: forward primer of SEQ ID NO: 27 and reverse primer of SEQ ID NO: 30, and probe of SEQ ID NO: 28;
viii) the G genotype for SNP marker 7 can be identified in a PCR by amplification of a nucleic acid fragment with a pair of oligonucleotide primers: forward primer of SEQ ID NO: 32 and reverse primer of SEQ ID NO: 35, and probe of SEQ ID NO: 33;
ix) the A genotype for SNP marker 8 can be identified in a PCR by amplification of a nucleic acid fragment with a pair of oligonucleotide primers: forward primer of SEQ ID NO: 37 and reverse primer of SEQ ID NO: 40, and probe of SEQ ID NO: 38; and/or
x) the A genotype for SNP marker 9 can be identified in a PCR by amplification of a nucleic acid fragment with a pair of oligonucleotide primers: forward primer of SEQ ID NO: 42 and reverse primer of SEQ ID NO: 45, and probe of SEQ ID NO: 43.

* * * * *